US010575951B2

(12) United States Patent
Johnson et al.

(10) Patent No.: US 10,575,951 B2
(45) Date of Patent: Mar. 3, 2020

(54) DELIVERY DEVICE AND METHODS OF USE FOR TRANSAPICAL DELIVERY OF REPLACEMENT MITRAL VALVE

(71) Applicant: Edwards Lifesciences CardiAQ LLC, Irvine, CA (US)

(72) Inventors: Garrett Dallas Johnson, Costa Mesa, CA (US); David Robert Landon, Costa Mesa, CA (US); Lindsay Lam, Costa Mesa, CA (US); Glen T. Rabito, Lake Forest, CA (US); Alexander H. Cooper, Costa Mesa, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 178 days.

(21) Appl. No.: 15/242,297

(22) Filed: Aug. 19, 2016

(65) Prior Publication Data
US 2017/0056169 A1 Mar. 2, 2017

Related U.S. Application Data

(60) Provisional application No. 62/210,302, filed on Aug. 26, 2015.

(51) Int. Cl.
*A61F 2/24* (2006.01)
*A61F 2/95* (2013.01)
(Continued)

(52) U.S. Cl.
CPC .......... *A61F 2/2433* (2013.01); *A61F 2/2418* (2013.01); *A61F 2/2436* (2013.01);
(Continued)

(58) Field of Classification Search
CPC ...... A61F 2/2427; A61F 2/243; A61F 2/2433; A61F 2/2436; A61F 2/2439; A61F 2/95;
(Continued)

(56) References Cited

U.S. PATENT DOCUMENTS 3,657,744 A 4/1972 Ersek
3,671,979 A 6/1972 Moulopoulos
(Continued)

FOREIGN PATENT DOCUMENTS

CA 2304325 A1 10/2000
CA 2827556 A1 7/2012
(Continued)

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
(Continued)

*Primary Examiner* — Kathleen S Holwerda
*Assistant Examiner* — Kankindi Rwego
(74) *Attorney, Agent, or Firm* — Knobbe Martens Olson & Bear LLP

(57) ABSTRACT

Devices, systems and methods are described for implantation of a prosthesis within a lumen or body cavity and delivery systems for delivering the prosthesis to a location for implantation. A delivery system can include a tether connected to a single directional handle knob for release of the prosthesis within the lumen or body cavity and retraction of the tether towards the handle.

12 Claims, 19 Drawing Sheets

(51) Int. Cl.
*A61M 25/10* (2013.01)
*A61F 2/966* (2013.01)

(52) U.S. Cl.
CPC ..... *A61F 2/2439* (2013.01); *A61F 2002/9511* (2013.01); *A61F 2002/9517* (2013.01); *A61F 2002/9665* (2013.01); *A61F 2230/0054* (2013.01); *A61F 2230/0065* (2013.01); *A61F 2250/0097* (2013.01); *A61F 2250/0098* (2013.01); *A61M 2025/1093* (2013.01)

(58) Field of Classification Search
CPC .......... A61F 2/954; A61F 2/958; A61F 2/962; A61F 2/966; A61F 2002/9505; A61F 2002/9511; A61F 2002/9517; A61F 2002/9522; A61F 2002/9534; A61F 2002/9665
See application file for complete search history.

(56) References Cited

U.S. PATENT DOCUMENTS

| | | | |
|---|---|---|---|
| 3,739,402 A | 6/1973 | Cooley et al. | |
| 4,056,854 A | 11/1977 | Boretos et al. | |
| 4,079,468 A | 3/1978 | Liotta et al. | |
| 4,204,283 A | 5/1980 | Bellhouse et al. | |
| 4,222,126 A | 9/1980 | Boretos et al. | |
| 4,265,694 A | 5/1981 | Boretos et al. | |
| 4,339,831 A | 7/1982 | Johnson | |
| 4,340,977 A | 7/1982 | Brownlee et al. | |
| 4,470,157 A | 9/1984 | Love | |
| 4,477,930 A | 10/1984 | Totten et al. | |
| 4,490,859 A | 1/1985 | Black et al. | |
| 4,553,545 A | 11/1985 | Maass et al. | |
| 4,777,951 A | 10/1988 | Cribier et al. | |
| 4,865,600 A | 9/1989 | Carpentier et al. | |
| 4,994,077 A | 2/1991 | Dobben | |
| 5,326,371 A | 7/1994 | Love et al. | |
| 5,332,402 A | 7/1994 | Teitelbaum | |
| 5,370,685 A | 12/1994 | Stevens | |
| 5,411,552 A | 5/1995 | Andersen et al. | |
| 5,415,667 A | 5/1995 | Frater | |
| 5,545,214 A | 8/1996 | Stevens | |
| 5,554,185 A | 9/1996 | Block et al. | |
| 5,697,382 A | 12/1997 | Love et al. | |
| 5,840,081 A | 11/1998 | Andersen et al. | |
| 5,855,601 A | 1/1999 | Bessler et al. | |
| 5,957,949 A | 9/1999 | Leonhardt et al. | |
| 6,086,612 A | 7/2000 | Jansen | |
| 6,113,631 A | 9/2000 | Jansen | |
| 6,168,614 B1 | 1/2001 | Andersen et al. | |
| 6,251,093 B1 | 6/2001 | Valley et al. | |
| 6,312,465 B1 | 11/2001 | Griffin et al. | |
| 6,358,277 B1 | 3/2002 | Duran | |
| 6,440,164 B1 | 8/2002 | DiMatteo et al. | |
| 6,458,153 B1 | 10/2002 | Bailey et al. | |
| 6,482,228 B1 | 11/2002 | Norred | |
| 6,527,800 B1 | 3/2003 | McGuckin, Jr. et al. | |
| 6,540,778 B1 | 4/2003 | Quiachon et al. | |
| 6,582,462 B1 | 6/2003 | Andersen et al. | |
| 6,610,088 B1 | 8/2003 | Gabbay | |
| 6,629,534 B1 | 10/2003 | St. Goar et al. | |
| 6,652,578 B2 | 11/2003 | Bailey et al. | |
| 6,676,698 B2 | 1/2004 | McGuckin, Jr. et al. | |
| 6,695,878 B2 | 2/2004 | McGuckin, Jr. et al. | |
| 6,712,836 B1 | 3/2004 | Berg et al. | |
| 6,716,207 B2 | 4/2004 | Farnholtz | |
| 6,729,356 B1 | 5/2004 | Baker et al. | |
| 6,730,118 B2 | 5/2004 | Spenser et al. | |
| 6,746,422 B1 | 6/2004 | Noriega et al. | |
| 6,749,560 B1 | 6/2004 | Konstorum et al. | |
| 6,767,362 B2 | 7/2004 | Schreck | |
| 6,780,200 B2 | 8/2004 | Jansen | |
| 6,790,229 B1 | 9/2004 | Berreklouw | |
| 6,790,230 B2 | 9/2004 | Beyersdorf et al. | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 7,186,265 B2 | 3/2007 | Sharkawy et al. | |
| 7,192,440 B2 | 3/2007 | Andreas et al. | |
| 7,198,646 B2 | 4/2007 | Figulla et al. | |
| 7,201,772 B2 | 4/2007 | Schwammenthal et al. | |
| 7,276,078 B2 | 10/2007 | Spenser et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| 7,462,191 B2 | 12/2008 | Spenser et al. | |
| 7,510,575 B2 | 3/2009 | Spenser et al. | |
| 7,524,330 B2 | 4/2009 | Berreklouw | |
| 7,553,324 B2 | 6/2009 | Andreas et al. | |
| 7,585,321 B2 | 9/2009 | Cribier | |
| 7,618,446 B2 | 11/2009 | Andersen et al. | |
| 7,621,948 B2 | 11/2009 | Herrmann et al. | |
| 7,628,805 B2 | 12/2009 | Spenser et al. | |
| 7,753,949 B2 | 7/2010 | Lamphere et al. | |
| 7,763,063 B2 * | 7/2010 | Arbefeuille ............... | A61F 2/07 623/1.11 |
| 7,803,185 B2 | 9/2010 | Gabbay | |
| 7,806,919 B2 | 10/2010 | Bloom et al. | |
| 7,815,673 B2 | 10/2010 | Bloom et al. | |
| 7,914,569 B2 | 3/2011 | Nguyen et al. | |
| 7,947,075 B2 | 5/2011 | Goetz et al. | |
| 7,972,378 B2 | 7/2011 | Tabor et al. | |
| 7,981,151 B2 | 7/2011 | Rowe | |
| 7,993,392 B2 | 8/2011 | Righini et al. | |
| 8,070,800 B2 | 12/2011 | Lock et al. | |
| 8,070,802 B2 | 12/2011 | Lamphere et al. | |
| 8,075,615 B2 | 12/2011 | Eberhardt et al. | |
| 8,080,054 B2 | 12/2011 | Rowe | |
| 8,092,520 B2 | 1/2012 | Quadri | |
| 8,109,996 B2 | 2/2012 | Stacchino et al. | |
| 8,118,866 B2 | 2/2012 | Herrmann et al. | |
| 8,136,218 B2 | 3/2012 | Millwee et al. | |
| 8,137,398 B2 | 3/2012 | Tuval et al. | |
| 8,157,852 B2 | 4/2012 | Bloom et al. | |
| 8,167,934 B2 | 5/2012 | Styrc et al. | |
| 8,182,530 B2 | 5/2012 | Huber | |
| 8,216,301 B2 | 7/2012 | Bonhoeffer et al. | |
| 8,219,229 B2 | 7/2012 | Cao et al. | |
| 8,220,121 B2 | 7/2012 | Hendriksen et al. | |
| 8,221,493 B2 | 7/2012 | Boyle et al. | |
| 8,226,710 B2 | 7/2012 | Nguyen et al. | |
| 8,236,045 B2 | 8/2012 | Benichou et al. | |
| 8,246,675 B2 | 8/2012 | Zegdi | |
| 8,252,051 B2 | 8/2012 | Chau et al. | |
| 8,303,653 B2 | 11/2012 | Bonhoeffer et al. | |
| 8,313,525 B2 | 11/2012 | Tuval et al. | |
| 8,323,335 B2 | 12/2012 | Rowe et al. | |
| 8,353,953 B2 | 1/2013 | Giannetti et al. | |
| 8,414,645 B2 | 4/2013 | Dwork et al. | |
| 8,444,689 B2 | 5/2013 | Zhang | |
| 8,449,599 B2 | 5/2013 | Chau et al. | |
| 8,454,685 B2 | 6/2013 | Hariton et al. | |
| 8,460,368 B2 | 6/2013 | Taylor et al. | |
| 8,470,023 B2 | 6/2013 | Eidenschink et al. | |
| 8,475,521 B2 | 7/2013 | Suri et al. | |
| 8,475,523 B2 | 7/2013 | Duffy | |
| 8,479,380 B2 | 7/2013 | Malewicz et al. | |
| 8,486,137 B2 | 7/2013 | Suri et al. | |
| 8,491,650 B2 | 7/2013 | Wiemeyer et al. | |
| 8,500,733 B2 | 8/2013 | Watson | |
| 8,500,798 B2 | 8/2013 | Rowe et al. | |
| 8,511,244 B2 | 8/2013 | Holecek et al. | |
| 8,512,401 B2 | 8/2013 | Murray, III et al. | |
| 8,518,096 B2 | 8/2013 | Nelson | |
| 8,518,106 B2 | 8/2013 | Duffy et al. | |
| 8,562,663 B2 | 10/2013 | Mearns et al. | |
| 8,579,963 B2 | 11/2013 | Tabor | |
| 8,579,964 B2 | 11/2013 | Lane et al. | |
| 8,579,965 B2 | 11/2013 | Bonhoeffer et al. | |
| 8,585,755 B2 | 11/2013 | Chau et al. | |
| 8,585,756 B2 | 11/2013 | Bonhoeffer et al. | |
| 8,591,570 B2 | 11/2013 | Revuelta et al. | |
| 8,597,348 B2 | 12/2013 | Rowe et al. | |

(56) References Cited

U.S. PATENT DOCUMENTS

| | | |
|---|---|---|
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,828,079 B2 | 9/2014 | Thielen et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,998,980 B2 | 4/2015 | Shipley et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,751 B2 | 7/2015 | Naor |
| 9,084,676 B2 | 7/2015 | Chau et al. |
| 9,125,738 B2 | 9/2015 | Figulla et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210307 A1 | 10/2004 | Khairkhahan |
| 2004/0215325 A1 | 10/2004 | Penn et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2006/0020327 A1 | 1/2006 | Lashinski et al. |
| 2006/0052867 A1 | 3/2006 | Revuelta et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0065011 A1* | 3/2008 | Marchand ............ A61F 2/2433 604/103.02 |
| 2008/0082159 A1 | 4/2008 | Tseng et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |

(56) References Cited

U.S. PATENT DOCUMENTS

| | | |
|---|---|---|
| 2009/0292350 A1 | 11/2009 | Eberhardt et al. |
| 2009/0306768 A1 | 12/2009 | Quadri |
| 2010/0049313 A1 | 2/2010 | Alon et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0264198 A1 | 10/2011 | Murray, III et al. |
| 2011/0288624 A1 | 11/2011 | Roeder et al. |
| 2012/0022639 A1 | 1/2012 | Hacohen et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0172915 A1* | 7/2012 | Fifer .................. A61F 2/013 606/200 |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0079872 A1* | 3/2013 | Gallagher ............. A61F 2/2436 623/2.11 |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310923 A1 | 11/2013 | Kheradvar et al. |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2015/0005863 A1 | 1/2015 | Para |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0051696 A1* | 2/2015 | Hou .................. A61F 2/2427 623/2.11 |
| 2015/0081009 A1 | 3/2015 | Quadri et al. |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0238315 A1* | 8/2015 | Rabito .................. A61F 2/2436 623/2.11 |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120676 A1* | 5/2016 | Gomes Nogueira ...... A61F 2/95 623/1.11 |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |

(56) References Cited

U.S. PATENT DOCUMENTS

| | | |
|---|---|---|
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1369098 A1 | 12/2003 |
| EP | 1472996 A1 | 11/2004 |
| EP | 1259194 B1 | 2/2005 |
| EP | 1734903 A1 | 12/2006 |
| EP | 1255510 B1 | 4/2007 |
| EP | 1827558 A2 | 9/2007 |
| EP | 1239901 B1 | 10/2007 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2398543 A1 | 12/2011 |
| EP | 1281375 B1 | 2/2012 |
| EP | 2496182 A1 | 9/2012 |
| EP | 2566416 A1 | 3/2013 |
| EP | 2319458 B1 | 4/2013 |
| EP | 2124826 B1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| WO | 1997049355 A1 | 12/1997 |
| WO | 0061034 A1 | 10/2000 |
| WO | 03063732 A2 | 8/2003 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010040009 A1 | 4/2010 |
| WO | 2010057262 A1 | 5/2010 |
| WO | 2010121076 A2 | 10/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015075708 A1 | 5/2015 |
| WO | 2015077274 A1 | 5/2015 |
| WO | 2015148241 A1 | 10/2015 |
| WO | 2016016899 A1 | 2/2016 |

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. of 2010.

Int'l. Search Report for PCT/US2016/048749, Completed Dec. 8, 2016.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. of 2006.

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Spillner, J. et al., "New Sutureless 'Atrial- Mitral-Valve Prosthesis' for Minimally Invasive Mitral Valve Therapy," Textile Research Journal, 2010, in 7 pages, Applicant believes this may have been available as early as Aug. 9, 2010.

Karimi, Houshang, et al., "Percutaneous Valve Therapies," SIS 2007 Yearbook, Chapter 11, pp. 1-11.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. of 2005.

(56) References Cited

OTHER PUBLICATIONS

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

Sondergaard, Lars, et al., "Transcatheter Mitral Valve Implantation: CardiAQ™," Applicant believes this may have been presented at EuroPCR 2013.

Sondergaard, Lars, "CardiAQ TMVR FIH—Generation 2," Applicants believe this may have been presented in 2014 at the TVT symposium.

CardiAQ Valve Technologies, "Innovations in Heart Valve Therapy," In3 San Francisco, Jun. 18, 2008, PowerPoint presentation in 19 slides.

Ratz, J. Brent, "LSI EMT Spotlight," May 15, 2009.

Ratz, J. Brent, "In3 Company Overview," Jun. 24, 2009.

"Company Overview," at TVT on Jun. 25, 2009.

Ruiz, Carlos E., "Overview of Novel Transcatheter Valve Technologies," Applicant believes this may have been presented on May 27, 2010 at EuroPCR.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

"Update," Applicant believes this may have been presented on Jun. 6, 2010 at TVT.

Mack, Michael, M.D., "Antegrade Transcatheter Mitral valve Implantation: A Short-term Experience in Swine Model," Applicant believes this may have been presented on May of 2011 at TVT.

Mack, Michael, M.D., "Antegrade Transcatheter Mitral valve Implantation: On-Going Experience in Swine Model," Applicant believes this may have been presented on Nov. of 2011 at TCT.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Quadri, Arshad M.D., "Transcatheter Mitral Valve Implantation (TMVI) (An Acute In Vivo Study)," Applicant believes this may have been presented on Sep. 22, 2010 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. of 2008.

Feldman, Ted, MD. "Prospects for Percutaneous Valve Therapies," Circulation 2007;116:2866-2877. Applicant believes that this may be available as early as Dec. 11, 2007.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. of 2014.

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

"CardiAQTM Valve Technologies reports Successful First-in-Human Trans-Apical implantation of its Second Generation Transcatheter Mitral Valve," CardiAQ Valve Technologies Press Release, May 20, 2014.

Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

(56) References Cited

OTHER PUBLICATIONS

Neovasc corporate presentation, Oct. 2009, available at http://www.neovasc.com/investors/documents/Neovasc-Corporate-Presentation-October-2009.pdf.

NJ350: Vote for Your Favorite New Jersey Innovations, Jun. 27, 2014, http://www.kilmerhouse.com/2014/06/nj350-vote-for-your-favorite-new-jersey-innovations/.

* cited by examiner

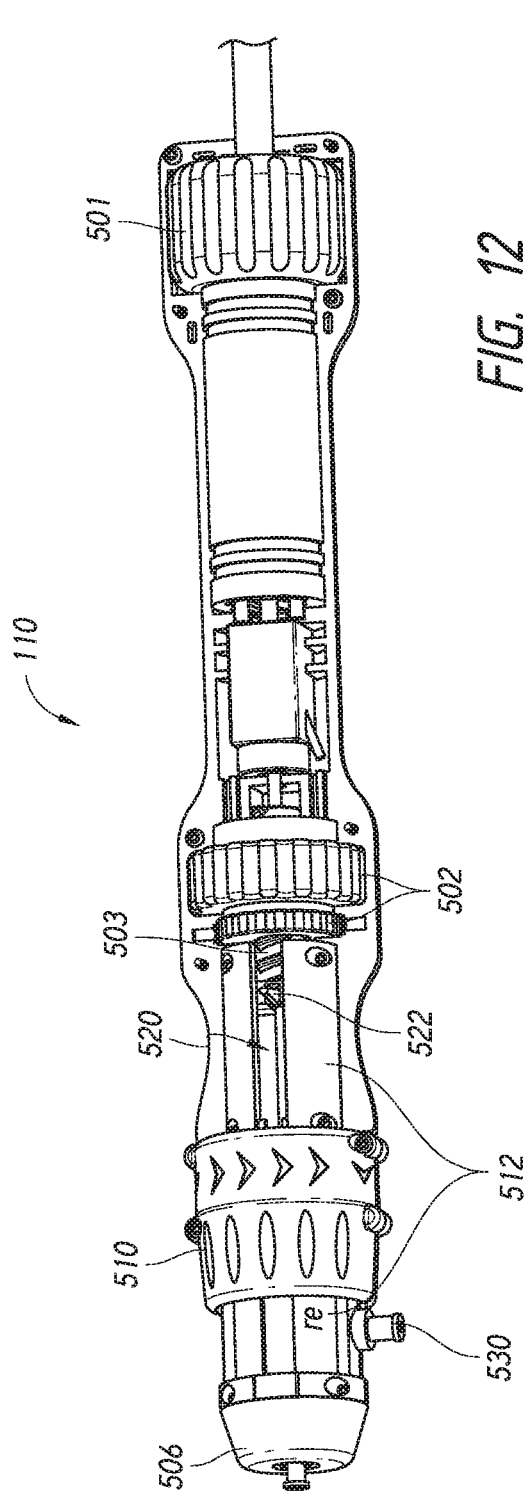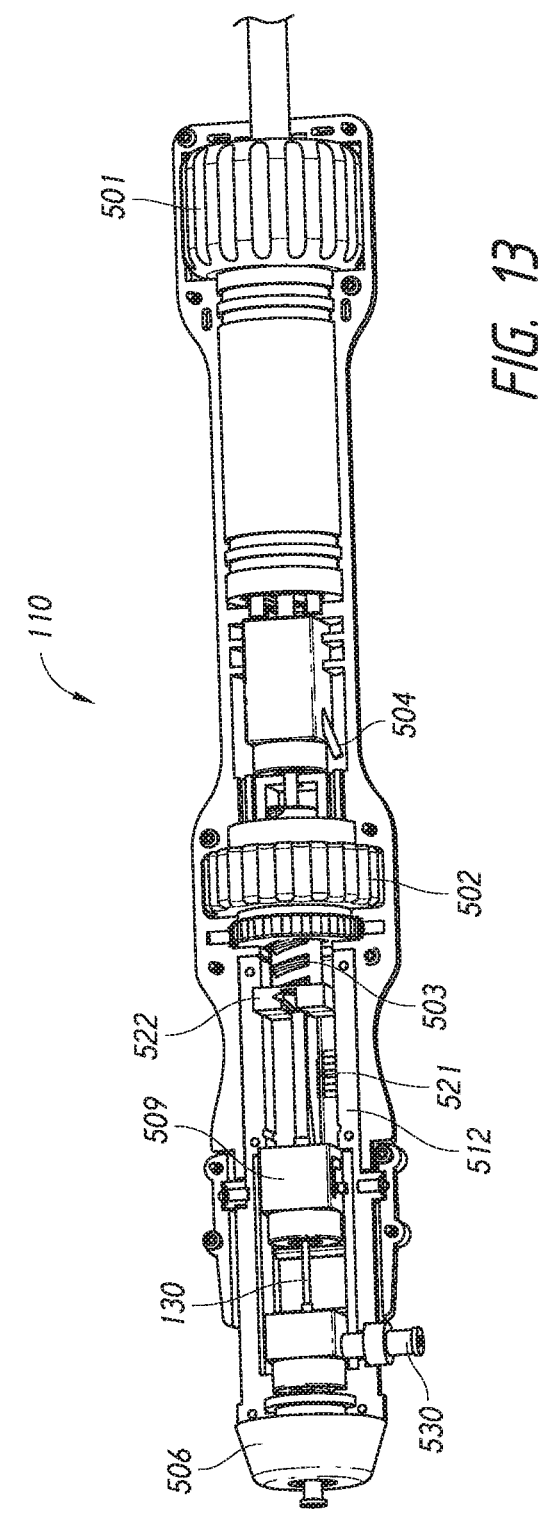

DELIVERY DEVICE AND METHODS OF USE FOR TRANSAPICAL DELIVERY OF REPLACEMENT MITRAL VALVE

INCORPORATION BY REFERENCE TO ANY PRIORITY APPLICATIONS

This application claims the benefit of U.S. Provisional Application No. 62/210,302, filed Aug. 26, 2015, tilted "PROSTHESIS, DELIVERY DEVICE AND METHODS OF USE", the entirety of which is incorporated herein by reference.

BACKGROUND

Field

Certain embodiments disclosed herein relate generally to prostheses for implantation within a lumen or body cavity and delivery devices for a prosthesis. In particular, the prostheses and delivery devices relate in some embodiments to replacement heart valves, such as replacement mitral heart valves.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

The present disclosure includes, but is not limited to, the following numbered embodiments.

Embodiment 1: A delivery system for controlled deployment of a collapsible implant, the delivery system comprising a handle at a proximal end of the delivery system, the handle comprising a tether control knob configured to control movement of a tether extending distally away from the handle, and an outer hollow member operably connected to the handle configured to at least partially restrain the implant in a collapsible configuration, wherein the tether extends through the outer hollow member to engage the implant when the implant is positioned within the outer hollow member, the outer hollow member being moveable relative to the implant to expose the implant at a body location while the tether keeps the implant radially restrained, wherein rotation of the tether control knob in a single direction first provides slack to the tether to controllably expand the implant at the body location, and continued rotation of the tether control knob in the single direction retracts the tether towards the handle.

Embodiment 2: The delivery system of Embodiment 1, wherein the tether is configured to unspool and spool in a cavity within the tether control knob.

Embodiment 3: The delivery system of any one of Embodiments 1-2, further comprising a replacement valve located within a distal portion of the outer hollow member, wherein the tether wraps around the replacement valve to prevent expansion of the replacement valve.

Embodiment 4: The delivery system of any one of Embodiments 1-3, further comprising a tether retention member located proximal to where the tether engages the implant, the tether retention member configured to hold a free end of the tether.

Embodiment 5: The delivery system of Embodiment 4, wherein the tether retention member comprises a c-lock provided on an inner shaft extending through the outer hollow member, the c-lock having a longitudinal slot covered by a locking shaft slidable over the inner shaft, the slot retaining the free end of the tether.

Embodiment 6: The delivery system of Embodiment 5, wherein rotation of the tether control knob translates the locking shaft proximally away from the c-lock to release the free end of the tether.

Embodiment 7: The delivery system of any one of Embodiments 5-6, wherein a proximal end of the locking shaft is operably connected to a block located within the handle and proximal of the tether knob, and rotation of the tether knob translates a screw proximally to abut and translate the block proximally.

Embodiment 8: The delivery system of any one of Embodiments 5-7, further comprising a centering ring on the locking shaft to center the locking shaft within the outer hollow member, the centering ring comprising at least one aperture through which the tether passes.

Embodiment 9: The delivery system of any one of Embodiments 1-8, wherein the handle comprises an auditory or visual indicator to provide a user a signal indicating a position of the tether.

Embodiment 10: A delivery system for controlled deployment of a collapsible implant, the delivery system comprising a handle comprising an outer housing and a sleigh located at least partially within the outer housing, a first elongate shaft operably connected to the housing and configured to cover at least a proximal end of the collapsible implant, a second elongate shaft located within the first elongate shaft and operably connected to the sleigh, a third elongate shaft located within the second elongate shaft and operably connected to the sleigh, a fourth elongate shaft located within the third elongate shaft and having a nose cone on a distal end thereof, the nose cone configured to radially restrain a distal end of the collapsible implant, the fourth elongate shaft is operably connected to the sleigh, wherein the sleigh is configured to translate relative to the housing from a distal to a proximal position, wherein translation of the sleigh from the distal to the proximal position translates the second, third, and fourth elongate shafts proximally so that the second, third, and fourth elongate shafts remain in the same position relative to one another in the distal and proximal position.

Embodiment 11: The delivery system of Embodiment 10, wherein the handle comprises a sleigh lock configured to prevent motion of the sleigh upon activation of the lock.

Embodiment 12: The delivery system of any one of Embodiments 10-11, further comprising a first shaft knob configured to translate the first elongate shaft distally and proximally, a second shaft knob configured to translate the second elongate shaft distally and proximally, and a fourth shaft knob configured to translate the fourth shaft distally and proximally, wherein each of the shaft knobs can move their respective shafts independent of one another.

Embodiment 13: The delivery system of any one of Embodiments 10-12, wherein the sleigh extends proximally from the handle in the proximal position.

Embodiment 14: A method of controllably releasing an implant from a collapsed configuration to an expanded configuration, the method comprising delivering an implant to an in situ target location while the implant is in a radially compacted state within an outer member of a delivery system, the implant comprising a first end, a second end, and a longitudinal axis extending between the first and second ends, wherein a tether encircles at least a portion of the implant, the tether configured to restrain the radial dimension of the implant, at least partially removing the outer member from the implant, wherein the tether restrains the radial dimension of the implant after the outer member is at least partially removed, rotating a tether knob in a handle of the delivery system in a first direction to loosen the tether encircling implant to cause at least the second end of the implant to controllably expand, rotating the tether knob in the first direction to release a free end of the tether, and rotating the tether knob in the first direction to remove the tether from the implant and to retract the free end of the tether proximally towards the handle.

Embodiment 15: The method of Embodiment 14, wherein the delivery system further comprises a locking shaft located within the outer member, an inner retention shaft located within the locking shaft, wherein an inner retention member is provided at a distal end of the inner retention shaft and a tether retention member is provided on the inner retention shaft proximal to the inner retention member, and a nose cone shaft located within the inner retention shaft and having a nose cone on a distal end of the nose cone shaft configured to radially restrain the first end of the implant.

Embodiment 16: The method of Embodiment 15, further comprising rotating a nose cone knob on the handle to move the nose cone distally to release the first end of the implant to cause the implant to expand to a fully expanded state.

Embodiment 17: The method of any one of Embodiments 15-16, wherein rotating the tether knob moves the locking shaft proximally to uncover the tether retention member.

Embodiment 18: The method of any one of Embodiments 15-17, further comprising pulling the nose cone, nose cone shaft, inner retention member, and inner retention member through the implant after the implant has been expanded.

Embodiment 19: The method of Embodiment 18, wherein the nose cone, nose cone shaft, inner retention member, and inner retention member are pulled through the implant while staying in the same relative position to one another.

Embodiment 20: The method of any one of Embodiments 14-19, wherein the implant comprises a replacement mitral valve comprising ventricular anchors and atrial anchors, wherein the ventricular anchors extend proximally toward the handle when the implant is an radially compacted state when covered by the outer member and restrained by the tether, and flip to extend distally when uncovered by the outer member.

Embodiment 21: The method of any one of Embodiments 14-19, wherein the implant is delivered to a native mitral valve through an aperture formed in an apex of a heart into the left ventricle.

Embodiment 22: A delivery system for controlled deployment of a replacement valve, such as a replacement mitral valve, the delivery system comprising a nose cone shaft having a proximal end and a distal end, a nose cone connected to the distal end of the nose cone shaft, wherein the nose cone comprises a proximally-facing opening to receive at least a first end of the replacement valve, an inner retention shaft having a proximal end and a distal end, the inner retention shaft being slidable over the nose cone shaft, an inner retention member connected to the distal end of the inner retention shaft, the inner retention member configured to engage the first end of the replacement valve, a tether retention member on the inner retention shaft positioned proximal to the inner retention member, a locking shaft having a proximal end and a distal end, the locking shaft being slidable over the inner retention shaft, wherein the locking shaft is configured to cooperate with the tether retention member to releasably engage a tether attached to the replacement valve, a centering ring located on the locking shaft and having a plurality of circumferentially-spaced apertures, each aperture configured to receive the tether, an outer elongate hollow member having a proximal end and a distal end, the outer elongate hollow member being slidable over the locking shaft, wherein the outer elongate hollow member is configured to cover at least the second end of the replacement valve when the first end of the replacement valve is engaged with the inner retention member and is covered by the nose cone, wherein the outer elongate hollow member is moveable relative to the nose cone to uncover the second end of the replacement valve while the first end of the replacement valve remains engaged to the inner retention ring and is covered by the nose cone, a tether having a free end configured to engage the tether retention member when the tether retention member is covered by the locking shaft, the tether extending distally from the tether retention member when the replacement valve is covered by the outer elongate hollow member and the nose cone to engage at least a portion of the replacement valve, the tether configured to extend proximally from the replacement valve through one of the apertures in the centering ring, and a handle configured to translate the nose cone shaft, the inner retention shaft, the locking shaft, and the outer elongate hollow member, the handle comprising a housing, a first knob configured to rotate to cause translation of the outer elongate hollow member proximally relative to the nose cone to uncover the second end of the replacement valve, a second knob configured to rotate to cause translation of the tether, wherein rotation of the knob in a single direction causes the tether to first unwind from a spool and then to be wound onto the spool, wherein unwinding of the tether from the spool causes a portion of the tether engaging at least a portion of the replacement valve to allow the replacement valve to controllably expand, and further winding of the tether onto the spool reverses movement of the tether and retracts the tether toward the handle, and wherein rotation of the second knob in the single direction causes proximal movement of the locking shaft relative to the inner retention shaft to release the free end of the tether from the tether retention member after the replacement valve is allowed to controllably expand, a third knob configured to rotate to cause translation of the nose cone shaft distally relative to the inner retention shaft to uncover the inner retention member and the first end of the replacement valve, a sleigh located within the housing and operably connected to proximal ends of the nose cone shaft, the inner retention shaft, and the locking shaft, wherein the sleigh is configured to translate from a distal position to a proximal position to move the nose cone shaft, the inner retention shaft and the locking shaft together, wherein the relative position of the nose cone shaft, the inner retention shaft, and the locking shaft are at the same position relative to one another when the sleigh is in the proximal position and the distal position, a single flush port extending through the housing and in fluid communication with the locking shaft and the inner retention shaft, and at least one indicator located on the housing, wherein the at least one indication is configured to provide auditory and/or visual cues regarding the position of the tether.

Embodiment 23: A delivery system for controlled deployment of a replacement valve, such as a replacement mitral valve, the delivery system comprising an elongate hollow member shaft having an elongate hollow member shaft lumen, a nose cone shaft extending through the elongate hollow member shaft lumen, a nose cone located on a distal end of the nose cone shaft, the nose cone having the nose cone shaft lumen extending therethrough, an inflation lumen, and a balloon located at least partially on an external surface of the nose cone, the balloon being in fluid communication with the inflation lumen and configured to expand and deflate, wherein the nose cone and the elongate hollow member shaft are configured to releasably retain the replacement valve.

Embodiment 24: The delivery system of Embodiment 23, further comprising an inflation source to inflate the balloon.

Embodiment 25: The delivery system of any one of Embodiments 23-24, wherein the elongate hollow member shaft is configured to at least partially cover the balloon in a deflated position.

Embodiment 26: The delivery system of any one of Embodiments 23-25, wherein the balloon extends distal to the nose cone in an inflated position.

Embodiment 27: The delivery system of any one of Embodiments 23-26, wherein the balloon does not extend distal to the nose cone in an inflated position.

Embodiment 28: The delivery system of any one of Embodiments 23-27, wherein the balloon forms a generally toroidal shape in an inflated position.

Embodiment 29: The delivery system of any one of Embodiments 23-28, wherein in a deflated position, the balloon is located on a tapered portion of the nose cone.

Embodiment 30: A method for the controlled deployment of a replacement valve, the method comprising inserting a distal end of a delivery system through an aperture in a heart into a left ventricle of the heart, inflating a balloon located on a nose cone of the delivery system, translating the delivery system distally to pass the expanded balloon through a mitral annulus and into a left atrium of the heart, and releasing a replacement valve from the delivery system into the mitral annulus.

Embodiment 31: The method of Embodiment 30, where a guidewire is not used.

Embodiment 32: The method of any one of Embodiments 30-31, where a separate balloon catheter is not used.

The method of any one of Embodiments 30-32, further comprising additionally inflating the balloon when located in the left atrium.

The method of any one of Embodiments 30-33, further comprising deflating the balloon and withdrawing the delivery system from the heart.

BRIEF DESCRIPTION OF THE DRAWINGS

FIG. 12 illustrates the handle of a delivery device with a portion of the housing removed.

FIG. 13 illustrates the handle of the delivery device with a portion of the housing and a portion of the sleigh removed.

DETAILED DESCRIPTION

The present specification and drawings provide aspects and features of the disclosure in the context of several embodiments of replacement heart valves, delivery devices and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery device, etc. should not be taken as limiting, and features of any one embodiment discussed herein can be combined with features of other embodiments as desired and when appropriate. While certain of the embodiments described herein are described in connection with a transapical delivery approach, it should be understood that these embodiments can be used for other delivery approaches. Moreover, it should be understood that certain of the features described in connection with some embodiments can be incorporated with other embodiments, including those which are described in connection with different delivery approaches.

Figure 1:
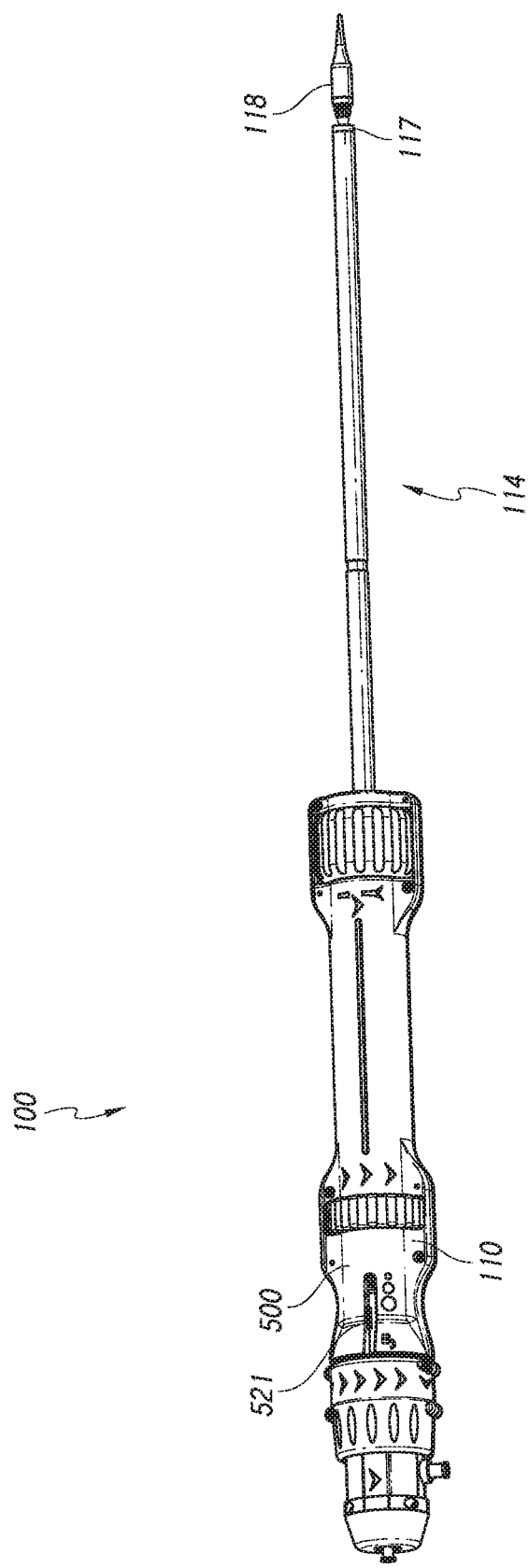
FIG. 1 illustrates an embodiment of a delivery device for a valve.

FIG. 1 illustrates an embodiment of a delivery device or system 100. The delivery system 100 can be used to deploy a prosthesis/implant, such as a replacement heart valve as described elsewhere in this specification, within the body. The delivery system 100 can receive and/or cover portions of the prosthesis such as a first end and second end of the implant. For example, the delivery system 100 may be used to deliver an expandable implant such as replacement mitral valve prosthesis 30 illustrated in FIG. 5, wherein the second end 14 is configured to be deployed or expanded before the first end 12. Replacement heart valves can be delivered to a patient's heart mitral valve annulus or other heart valve location in various ways, such as by open surgery, minimally-invasive surgery, and percutaneous or transcatheter delivery through the patient's vasculature. The delivery system 100 illustrated in FIG. 1 can be relatively short to more easily be used in an open heart procedure or other more direct procedures than the percutaneous procedure starting at the leg. At the same time, the delivery system 100 can still be relatively flexible to allow, for example, advancement through the pulmonary veins or the wall of the left atrium and then bending of the delivery device for proper placement at the mitral valve. In some embodiments, the delivery system 100 is particularly suitable for delivering a replacement heart valve to a mitral valve location through a transapical approach (e.g., through the apex of the heart).

With reference first to the embodiment illustrated in FIG. 1, the delivery system 100 can include a handle 110 and a plurality of sheaths and/or shafts such as the illustrated outer elongate hollow member shaft 114. As will be described in further detail below, the plurality of shafts can be sized and shaped to be slidable relative to each other. Accordingly, it should be understood that one or more of the plurality of shafts can be concentric with respect to another of the shafts to facilitate slidable movement of the shafts relative to each other. The plurality of shafts can be coupled to one or more other components of the delivery system 100. In some embodiments, the handle 110 can include a plurality of switches, levers, or other actuatable mechanisms which can be used to control the movement of the one or more shafts of the delivery system 100 and/or to control the operation of other components of the delivery system 100. A discussion of the handle 110 can be found below.

With continued reference to the embodiment of FIG. 1, the delivery system 100 can include an outer elongate hollow member such as the outer elongate hollow member shaft 114 having a proximal and distal end. As used to describe the components of the delivery system, "proximal" refers to a location of the component that is closer to the handle 110, and "distal" refers to a location of the component that is further from the handle 110. In some embodiments, the proximal end of the outer elongate hollow member shaft 114 can be coupled to the handle 110. In some embodiments, the outer elongate hollow member shaft 114 can be fixed relative to the handle 110. In some embodiments, the outer elongate hollow member shaft 114 can be movable relative to the handle 110. The outer elongate hollow member shaft 114 can include sheath and/or capsule, and may be made of one or multiple members. The outer elongate hollow member shaft 114 can have the same diameter from the proximal to distal end, or the diameter may vary. The outer elongate hollow member shaft 114 can be formed from a variety of materials, including ePTFE and PEEK, as well as other biocompatible materials. Further, the outer elongate hollow member shaft 114 can include a coating, such as a hydrophilic coating.

In some embodiments, the outer elongate hollow member shaft 114 can cover at least a portion of a collapsed or compressed implant 30 while the implant 30 is being delivered to the deployment site. For example, the outer elongate hollow member shaft 114 can cover at least the second end 14 of the implant 30 while the first end 12 of the implant 30 is received within a hollow nose cone 118, described further below. In some embodiments, the outer elongate hollow member shaft 114 can also cover the first end 12 of the implant 30. The outer elongate hollow member shaft 114 can be sized and shaped such that the outer elongate hollow member shaft 114 can retain the implant 30 in a compressed state as it is delivered to the deployment site. Accordingly, the outer elongate hollow member shaft 114 can function as a capsule for receiving the implant 30. As shown in the illustrated embodiment, the outer elongate hollow member shaft 114 can have a constant or substantially constant outer diameter throughout the entirety, or a substantial portion of the entirety, of its length. The outer elongate hollow member shaft 114 can be moveable relative to the nose cone 118 to uncover the second end 14 of the implant 30 while the first end 12 of the implant 30 remains engaged to an inner retention member (described below) within the nose cone 118 and remains covered by the nose cone 118.

Figure 5:
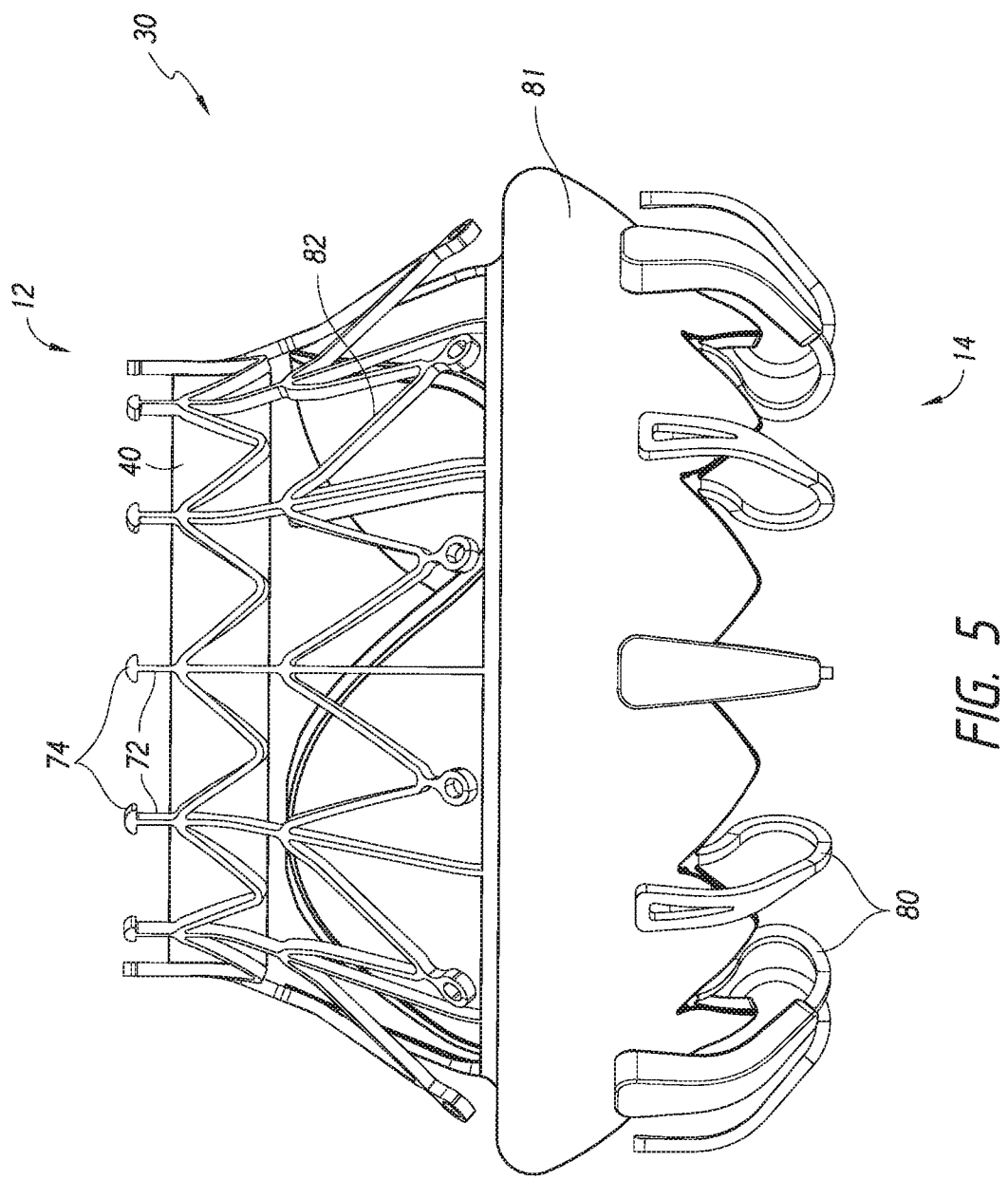
FIG. 5 illustrates an embodiment of a replacement valve.

FIG. 5 shows an example of the implant 30 that can be inserted into the delivery system 100. The implant 30 can take any number of different forms. A particular example of frame for an implant 30 is shown herein, though it will be understood that other designs can also be used. The implant 30 can include one or more sets of anchors, such as ventricular anchors 80 extending proximally when the implant frame is in an expanded configuration and atrial anchors 82 extending distally when the implant frame is in an expanded configuration. The implant 30 can also include struts 72 having mushroom-shaped tabs 74 on the ends at the first side 12. Further, the implant 30 can be at least partially surrounded by an annular flap 81 between the ventricular anchors 82 and the atrial anchors 82 near the second side 14. This flap 81 can wrap around the frame of the implant 30 and help position the implant 30 in the desired position in the body.

Additional details and example designs for an implant are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, the entirety of these patents and publications are hereby incorporated by reference and made a part of this specification. Further details and embodiments of a replacement heart valve or prosthesis and its method of implantation are also described in U.S. patent application Ser. No. 14/716,507, filed May 19, 2015, and Ser. No. 15/141,684, filed Apr. 28, 2016, the entirety of each of which is hereby incorporated by reference and made a part of this specification.

The outer elongate hollow member shaft 114 can include a marker 117 positioned proximate the distal end, such as a radiopaque marker that allows for visualization by a physician. In some embodiments, the outer elongate hollow member shaft 114 can be formed of multiple layers of material, such that the outer elongate hollow member shaft 114 includes at least a first radial portion and a second radial portion. This can advantageously allow for the use of two types of material for the outer elongate hollow member shaft 114. For example, at least a portion of the first portion can be positioned radially outward from the second portion relative to a central longitudinal axis of the outer elongate hollow member shaft 114. The first portion, which may be considered an outer layer, can be formed from a relatively rigid material, such as PEBAX, ULTEM, PEAK and any other biocompatible material as desired. This can advantageously provide some degree of rigidity for the outer portion of the elongate hollow member shaft 114. The second portion, which may be considered an inner layer, can be formed from a more compliant material, such as PTFE, ePTFE and any other biocompatible material as desired. This can advantageously provide a more compliant inner surface for the outer elongate hollow member shaft 114, which can be beneficial when contacting other components of the delivery system 100 and the prosthesis. In some embodiments, the second portion can be a liner which is applied to the first portion.

While the outer elongate hollow member shaft 114 can be formed with multiple portions formed from multiple materials, it is also contemplated that the outer elongate hollow member shaft 114 can be a formed from a single material.

Figure 2:
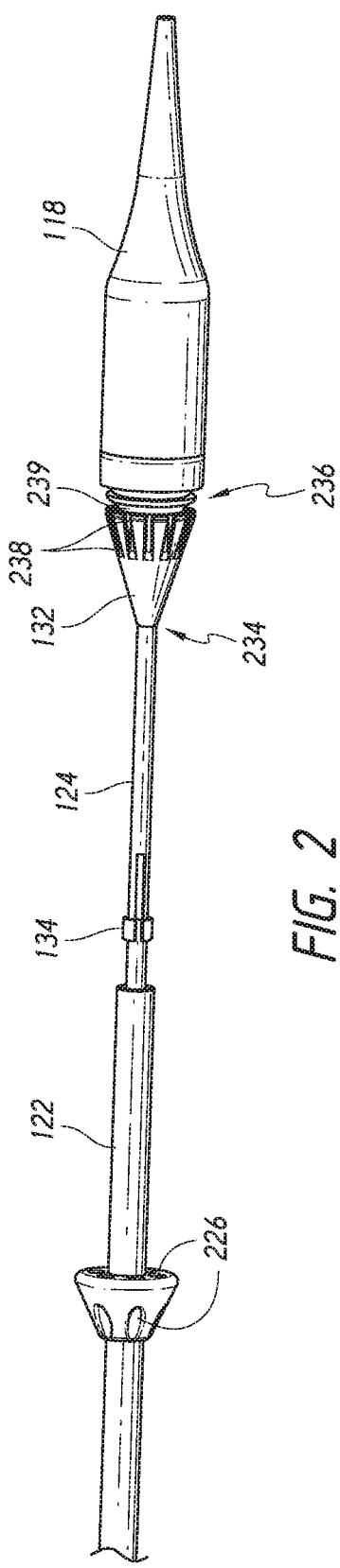
FIG. 2 illustrates a distal end of an embodiment of the delivery device.
Figure 3:
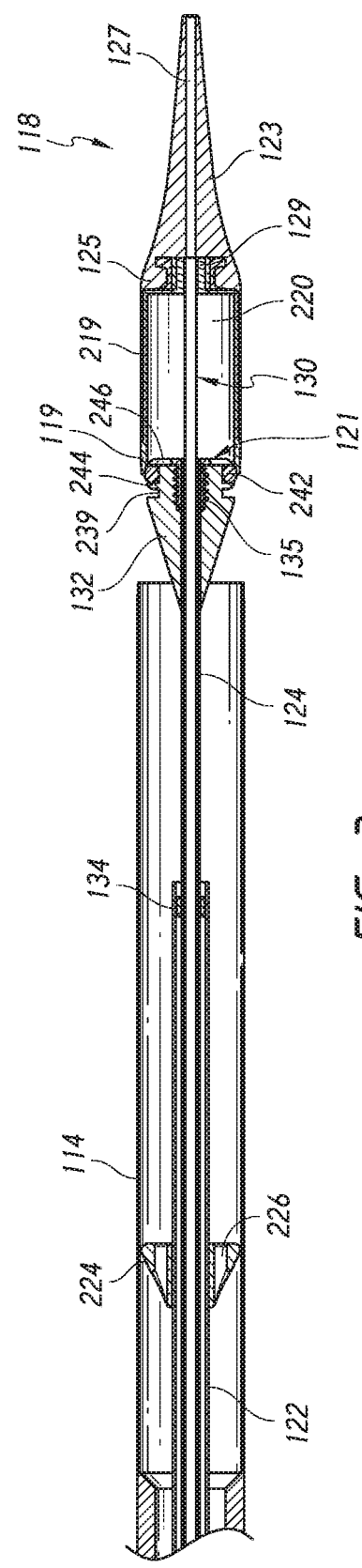
FIG. 3 illustrates a cross section of an embodiment of the delivery device.
Figure 4:
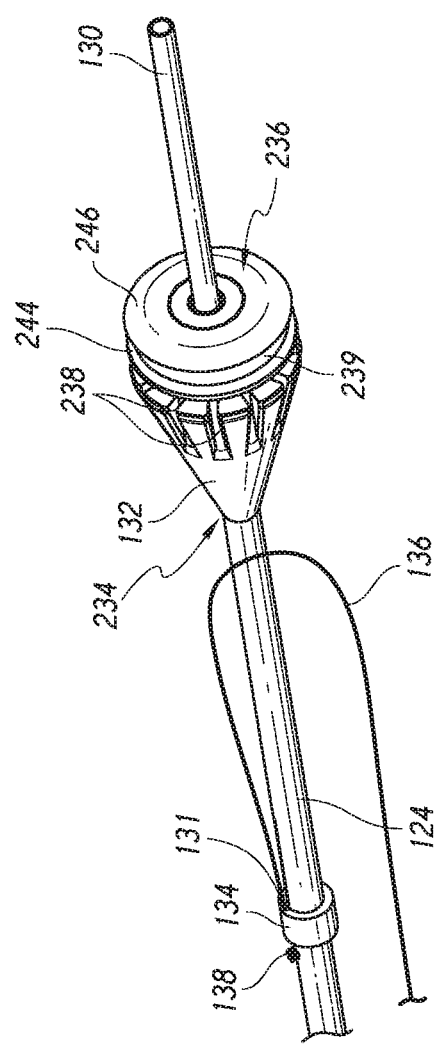
FIG. 4 illustrates a distal end of an embodiment of the delivery device of FIGS. 1-3 with the nosecone removed.

With reference now to FIGS. 2-4 (where FIGS. 2 and 4 illustrate delivery system 100 without the outer elongate hollow member shaft 114 being shown), the delivery system 100 can include, from radially inside to radially outside, a nose cone shaft 130, an inner retention shaft 124 provided concentrically over the nose cone shaft 130, and a locking shaft 122 provided concentrically over the inner retention shaft 124. Each of the shafts can move axially with relation to one another, and in some embodiments, some of these shafts may be moved together. In FIGS. 2 and 4, it will be noted that the locking shaft 122 has been withdrawn proximally for convenience of viewing portions of the inner retention shaft 124, while in FIG. 3, the locking shaft 122 is illustrated as being advanced more distally along the inner retention shaft 124. FIG. 4 as illustrated has the nose cone 118 removed.

The nose cone shaft 130 has a proximal end operably connected to the handle 110 and a distal end coupled to nose cone 118. The nose cone shaft 130 may be hollow along its length to receive a guidewire. Nose cone 118 comprises an elongate, hollow portion 119 with a proximally facing opening 121, and a tapered distal portion 123 (as shown in FIG. 3). The nose cone shaft 130 may be coupled to the nose cone 118 at a distal end of the elongate, hollow portion 119, such that the nose cone shaft 130 extends through the proximal opening 121 and ends at the intersection 125 between the elongate, hollow portion 119 and the tapered distal portion 123 at nose cone lock 129. The nose cone 118 can further contain a lumen 127 extending from the distal end of the nose cone shaft 130 to the distal end of the nose cone 118, which can allow a guide wire to pass through. The nose cone 118 can be formed from a relatively rigid, high durometer material. The nose cone 118, including both the elongate, hollow portion and the tapered, distal portion, can have a length, measured from the distalmost end to a proximalmost end, of between approximately 5 mm to 50 mm, between approximately 10 mm to approximately 40 mm, between approximately 15 mm to approximately 25 mm, approximately 20 mm, any other lengths within these ranges, and any other lengths as desired.

As shown in FIGS. 2 and 3, the tapered distal portion can have a concave outer surface thereby forming a more defined distal tip of the nose cone 118. As shown more clearly in the cross-section of FIG. 3, the nose cone 118 can include an outer portion 219 and a nose cone insert 220, the nose cone insert 220 being generally tubular in shape and forming a cavity within the nose cone 118 and the outer portion 219 forming the general shape of the nose cone 118 and extending from the proximal to the distal portion of the nose cone 118. The nose cone insert 220 may only be located in the proximal portion of the nose cone 118. This can advantageously allow for the use of two types of material for the nose cone 118. For example, as shown in the illustrated embodiment, at least a portion of the outer portion 219 can be positioned radially outward from the nose cone insert 220 relative to a central longitudinal axis of the nose cone 118. The outer portion 219 can be formed from a lower durometer material such as urethane, PEBAX, polysilicone and any other biocompatible material as desired. The nose cone insert 220 can be formed from higher durometer materials such as stainless steels, titanium, and any other biocompatible material as desired. This can advantageously provide additional structural support for the nose cone 118. The nose cone insert 220 can have an inner diameter of about 0.2, 0.25, 0.3, 0.343, 0.35, or 0.4 inches and a length of about 0.6, 0.65, 0.7, 0.709, 0.75, or 0.8 inches. The nose cone insert 220 can have an inner diameter of greater than about 0.2, 0.25, 0.3, 0.343, 0.35, or 0.4 inches and a length of greater than about 0.6, 0.65, 0.7, 0.709, 0.75, or 0.8 inches. The nose cone insert 220 can have an inner diameter of less than about 0.2, 0.25, 0.3, 0.343, 0.35, or 0.4 inches and a length of less than about 0.6, 0.65, 0.7, 0.709, 0.75, or 0.8 inches. In some embodiments, the nose cone insert 220 can include threading for attachment to a shaft, such as nose cone shaft 130. The threading can be located towards the distal end of the nose cone 118, and can be a separate piece such as nose cone lock 129. In some embodiments, the outer portion 219 can be overmolded onto the nose cone insert 220 and/or attached using mechanical fasteners such as screws, bolts, rivets, and threaded couplings, chemical fasteners, such as adhesives, or other types of fastening techniques such as welding. In some embodiments, the nose cone 118 can be a single unit formed from a single material. Further, the nose cone 118 can be flexible and self-dilating.

With reference particularly to the cross-sectional view of FIG. 3, the outermost diameter of the nose cone 118, such as the outer diameter of the elongate, hollow portion 119, can be similar to, or equal to, the outer diameter of an outer shaft and/or outer component, such as the outer elongate hollow member shaft 114. As shown in the illustrated embodiment, the elongate, hollow portion 119 has an outer diameter which is similar to that of the outer elongate hollow member shaft 114. This can form a generally smooth transition in diameter between the nose cone 118 and the outer shaft and/or the outer component if and when the nose cone 118 is brought into contact with the outer shaft and/or the outer component. In some embodiments, the elongate, hollow portion 119 of the nose cone 118 can have an outer diameter of approximately 31 Fr or 32 Fr and the outer shaft and/or outer component can have an outer diameter of approximately 31 Fr or 32 Fr.

In some embodiments, the outer diameter of the nose cone 118, such as the elongate, hollow portion 119, can be similar to, or equal to, the inner diameter of the outer elongate hollow member shaft 114 such that nose cone 118 can be partially received within the outer elongate hollow member shaft 114. In some embodiments, the elongate, hollow portion of the nose cone 118 can have an outer diameter of approximately 30 Fr and the outer shaft and/or outer component can have an inner diameter of approximately 30 Fr. In some embodiments, the outer shaft can be an outermost shaft of the delivery system.

With continued reference to the embodiment of FIGS. 2-4, the inner retention shaft 124 is slidable over the nose cone shaft 130, such that the nose cone shaft 130 can be moved within the inner retention shaft 124 and the inner retention shaft 124 can be moved over the nose cone shaft 130. The distal end of the inner retention shaft 124 can be coupled to at least a portion of an inner retention member 132 that can be positioned within and be removed from the proximally-facing opening of the nose cone 118. The inner retention member 132 can be attached to the inner retention shaft 124 with threading 135 (shown in FIG. 3). Further, the inner retention member 132 can have an elongated and proximally tapered design. The inner retention member 132 can be formed of a single material, or a plurality of different materials.

Further, as shown in FIG. 2, the inner retention member 132 can have a proximal end 234 and a distal end 236 with a plurality of slots 238 sized and shaped to receive portions of a first end 12 of the implant 30 positioned proximate the proximal end 234. For example, the inner retention member 132 may comprise a ring surrounding the inner retention shaft 124 with slots 238 configured to receive longitudinally-extending struts 72 on the implant 30 that are located just distal to enlarged, mushroom-shaped locking tabs 74 (shown in FIG. 5). Slots 238 can be circumferentially-spaced from each other extend along a longitudinal axis of the inner retention member 232. In some embodiments, the inner retention member 132 can include a cavity 239 positioned distal the slots 238. The cavity 239 can be sized and shaped to receive portions of the first end 12 of the implant 30, such as the locking tabs 74. As shown in the illustrated embodiment, the cavity 239 can have an annular shape or may be considered to extend circumferentially around the inner retention member 132. In some embodiments, the inner retention member 132 can include a taper towards the proximal end 234. This can facilitate removal of the inner retention member 132 from the heart by reducing the diameter at the proximalmost end of the inner retention member 132 and reducing the likelihood of snagging on tissue.

Figure 6:
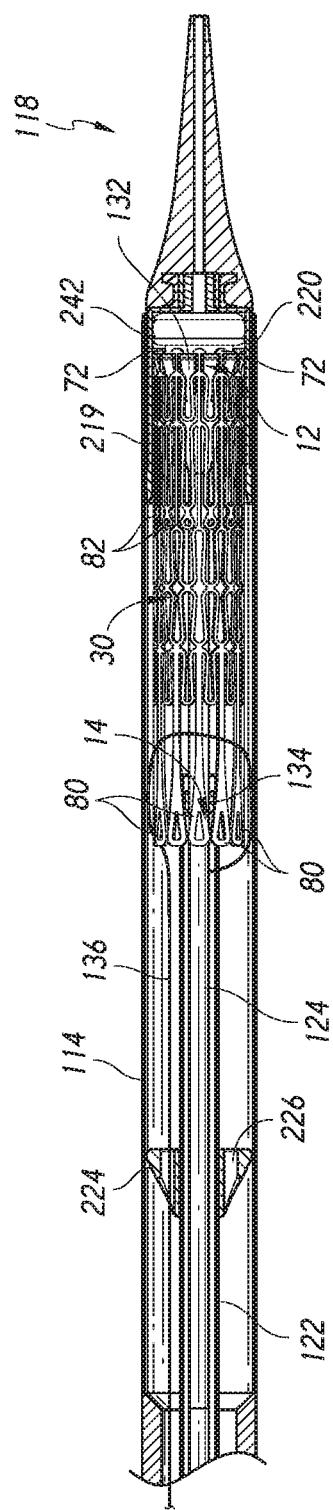
FIG. 6 illustrates a cross section of an embodiment of the delivery device including the replacement valve of FIG. 5.

The inner retention shaft 124 can cooperate with the inner retention member 132 and the nose cone 118 to release a first end of the prosthesis from the nose cone 118. As shown in FIG. 6, the first end 12 of the implant 30 can be placed in a compressed state such that the first end 12 of the implant 30 is retained between the inner retention member 132 and the nose cone 118 when the inner retention member 132 is received within and covered by the nose cone 118. Proximal movement of the inner retention shaft 124 with respect to the nose cone 118 can result in proximal movement of the inner retention member 132 relative to the nose cone 118 which can release the first end 12 of the prosthesis 30 from the nose cone 118. Similarly, distal movement of the nose cone 118 relative to the inner retention shaft 124, and thus the inner retention member 132, can also release the first end 12 of the prosthesis 30 from the nose cone 118. If the implant 30 is not covered by the outer elongate hollow member shaft 114, once the inner retention shaft 124 is moved relative to the nose cone 118 to uncover the first end 12 of the implant 30, the first end 12 of the implant 30 may self-expand from its compressed state to an expanded configuration.

Further, the inner retention member 132 can include a circumferential cavity proximate the distal end 236. The cavity can be formed between one or more radially extending protrusions, such as ridges 244, 246, illustrated in FIG. 3. As shown in the illustrated embodiment of FIGS. 2 and 3, the cavity can have an annular shape. A compressible member 242, such as an O-ring, can be received at least partially within the cavity 240 as shown in FIG. 3. The compressible member 242 can act as a seal between the inner retention member 132 and the nose cone 118 to keep the components together during retraction and allow for smooth sheathing into the outer elongate hollow member shaft 114. Moreover, the compressible member 242 can ensure that there is no gap between the nose cone 118 and the inner retention member 132 to prevent a portion of the implant 30 from being caught during removal of the nose cone 118 and inner retention member 132. Further, the compressible member 242 can keep the nose cone 118 from coming into contact with the inner retention member 132.

Further, the inner retention shaft 124 can include a tether retention member 134 proximal to the inner retention member 132. As shown in the illustrated embodiment of FIG. 4, the tether retention member 134 can be a C-lock mounted on the inner retention shaft 124 having a longitudinal opening or slot 131 through which a tether or lasso 136, such as a nitinol wire having a suture crimped on the end, can pass. In order to retain the tether 136 within the tether retention member 134, the end 138 of the tether 136 can be sized and shaped such that the end 138 is prevented from passing distally through the opening of the tether retention member 134 when the end 138 is located proximal to the opening. For example, the end 138 of the tether 136 can be knotted such that at least one dimension of the end 138 prevents the end 138 from passing distally through the opening. The locking shaft 122, described below, will further restrain the tether 136 from moving radially outwards through the slot in the tether retention member 134 and thus the locking shaft 122 and tether retention member 134 cooperate to releasably engage the tether 136.

In the illustrated embodiment, provided over the inner retention shaft 124 is a locking shaft 122. In some embodiments, inner retention shaft 124 can be sized and shaped such that inner retention shaft 124 is slidable within the locking shaft 122. For example, in some embodiments, the inner retention shaft 124 can be moved within the locking shaft 122. In some embodiments, the locking shaft 122 can be moved over the inner retention shaft 124. As shown in FIGS. 2 and 3, the locking shaft 122 may slide over the inner retention shaft 124 and cover the tether retention member 134. The locking shaft 122 can cooperate with the tether retention member 134 to retain a tether, or lasso, 136 (shown in FIG. 4) attached to an implant 30 until the locking shaft 122 is translated proximally to release the tether 136. Moreover, locking shaft 122 can be sized and shaped such that the outer elongate hollow member shaft 114 is slidable over the locking shaft 122.

When the tether 136 is positioned in the tether retention member 134, the tether 136 can be released by translating the locking shaft 122 proximally. Thus, a radially outwards tension force will pull the end 138 of the tether 136 out of the tether retention member 134. The tether 136 can be tensioned and angled such that the tether 136 would pass over the tether retention member 134 when tether retention member 134 is uncovered from the locking shaft 122. It should be understood that other mechanisms can be used for tether retention assembly in lieu of the lock and tether retention member 134 including, but not limited to, clamps which engage the tether 136. As shown in FIG. 6, the tether 136 can engage at least a portion of the prosthesis, such as the second end 14 of the implant 30. For example, in some embodiments, the tether 136 can extend distally from the tether retention member 134, wrap around at least some portion of the implant 30 when the implant is compressed within outer elongate hollow member shaft 114 and nose cone 118, and extend at least proximally through the outer elongate hollow member shaft 114. The end opposite end 138 can be attached to a component of the delivery system 100 such that the tether 136 can be retracted into the delivery system 100 upon release of the tether 136 from the tether retention assembly 128.

In some embodiments such as that illustrated in FIG. 3, the locking shaft 122 can include a centering ring/radial protrusion 224, such as an annular and/or tapered disc, positioned proximal to its distal end. The centering ring 224 can assist in maintaining the locking shaft 122 in a desired radial alignment relative to the shaft within which the locking shaft 122 is positioned (e.g., the outer elongate hollow member shaft 114). For example, as shown in the illustrated embodiment, the centering ring 224 can assist in maintaining concentricity between the locking shaft 122 and another shaft such as the outer elongate hollow member shaft 114. The centering ring 224 can be tapered on its proximal end, as shown, for ease of the centering ring 224 entering the outer elongate hollow member shaft 114 during retrieval of the system 10. In some embodiments, the centering ring 224 can include a plurality of apertures/guide members 226 positioned circumferentially around the locking shaft 122 and circumferentially spaced from one another for the tether, wire or suture 136 to pass through. Any one of the guide members 226 can be used for the tether 136 as is convenient for a user. As shown in the illustrated embodiment, each guide member 226 can be formed as a hole or aperture on the centering ring 224.

The embodiments of FIGS. 6-12 illustrates steps of a method of operating the delivery system 100 and releasing an intralumenal frame assembly, such as implant 30, to intralumenal tissue at an in situ target location. The steps of this method can be carried out while the implant is in a radially compacted state within the outer elongate hollow member shaft 114. In some embodiments, the longitudinal axis of the implant 30, which runs between the first 12 and second ends 14 of the implant 30, can be parallel to and/or concentric with the longitudinal axis of one or more shafts of the delivery system 100. The steps of this method can be used to transapically deliver a replacement heart valve to a mitral valve location.

FIG. 6 shows a cross section of the delivery system 100 with the implant 30 located in the delivery position. For ease of illustration, the implant 30 is shown in FIG. 6 with only its metal frame illustrated. As shown, the outer elongate hollow member shaft 114 covers the implant 30, thus preventing expansion of the implant 30, in particular the second end 14. Further, the ventricular anchors 80 of the implant extend proximally toward the handle 110, with the outer elongate hollow member shaft 114 radially restraining the ventricular anchors 80 pointing proximally. The outer elongate hollow member shaft 114 extends distally to the nose cone 118, which covers the inner retention member 134. The first end 12 of the implant 30 is positioned within the inner retention member 134, with struts 72 located within the slots of the inner retention member 134 and covered by the nose cone 118. Further, the tether 136 extends distally from the handle 110, within the outer elongate hollow member shaft 114, through one of the guide members 226, and is wrapped around the implant, more preferably wrapping around the ventricular anchors 80 that extend proximally. The tether 136 then extends proximally to the tether retention member 134 located within the locking shaft 122, where the end of the tether 136 is locked in position as described above.

Figure 7:
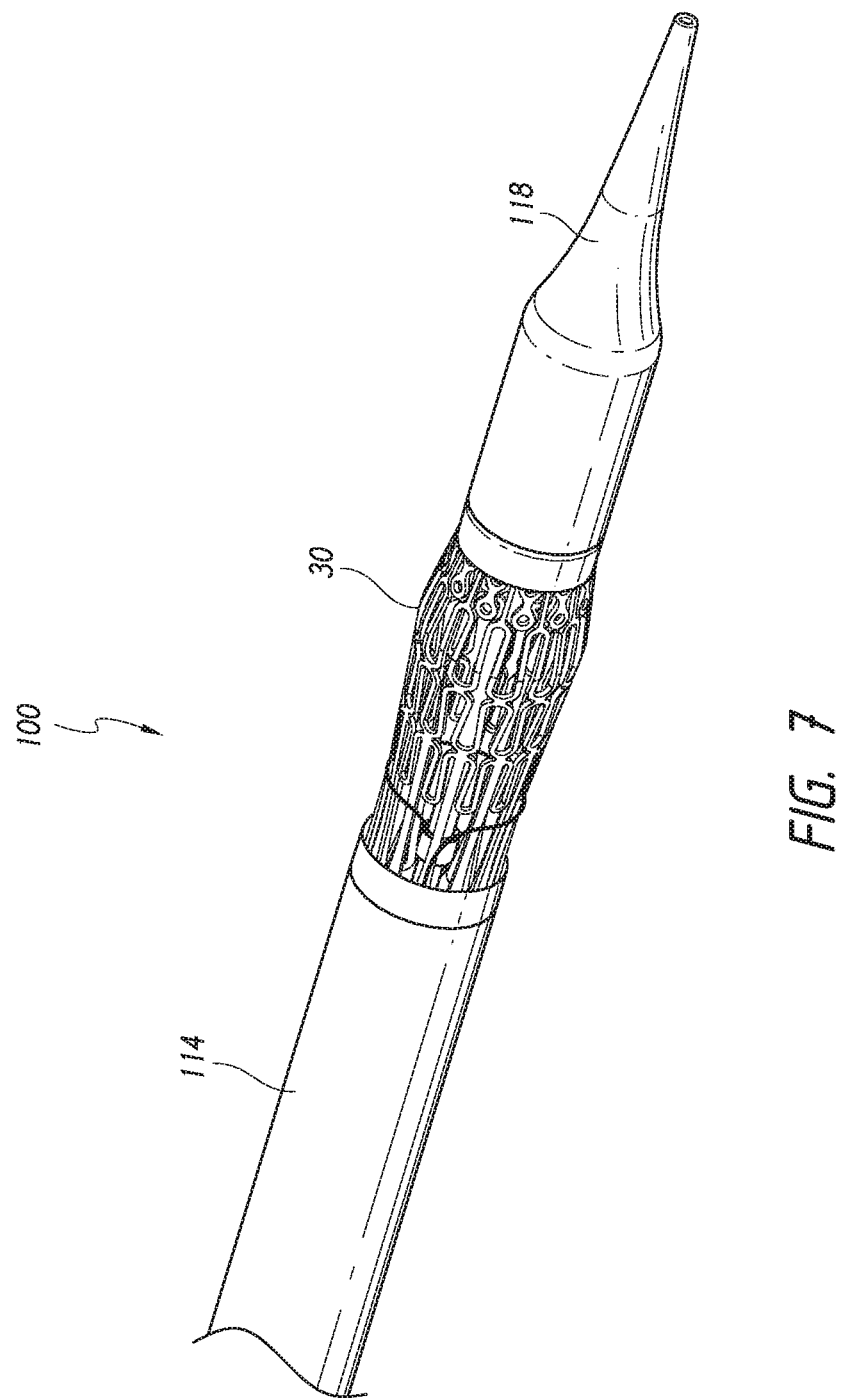
FIGS. 7-11 illustrate an embodiment of an implantation procedure of a replacement valve using the delivery device.

With reference next to the step of FIG. 7, once the delivery system 100 has positioned the implant at the in situ target location, the outer elongate hollow member shaft 114 can be moved relatively away from the nose cone 118, either by proximally retracting the outer elongate hollow member shaft 114 and/or distally advancing the nose cone 118, nose cone shaft 130, inner retention shaft 124, and inner retention member 132, to uncover at least a portion of the implant 30, in particular the second end 14 of the implant 30. As shown in FIG. 7, there may be a slight bulge in the implant 30 during this phase.

Figure 8:
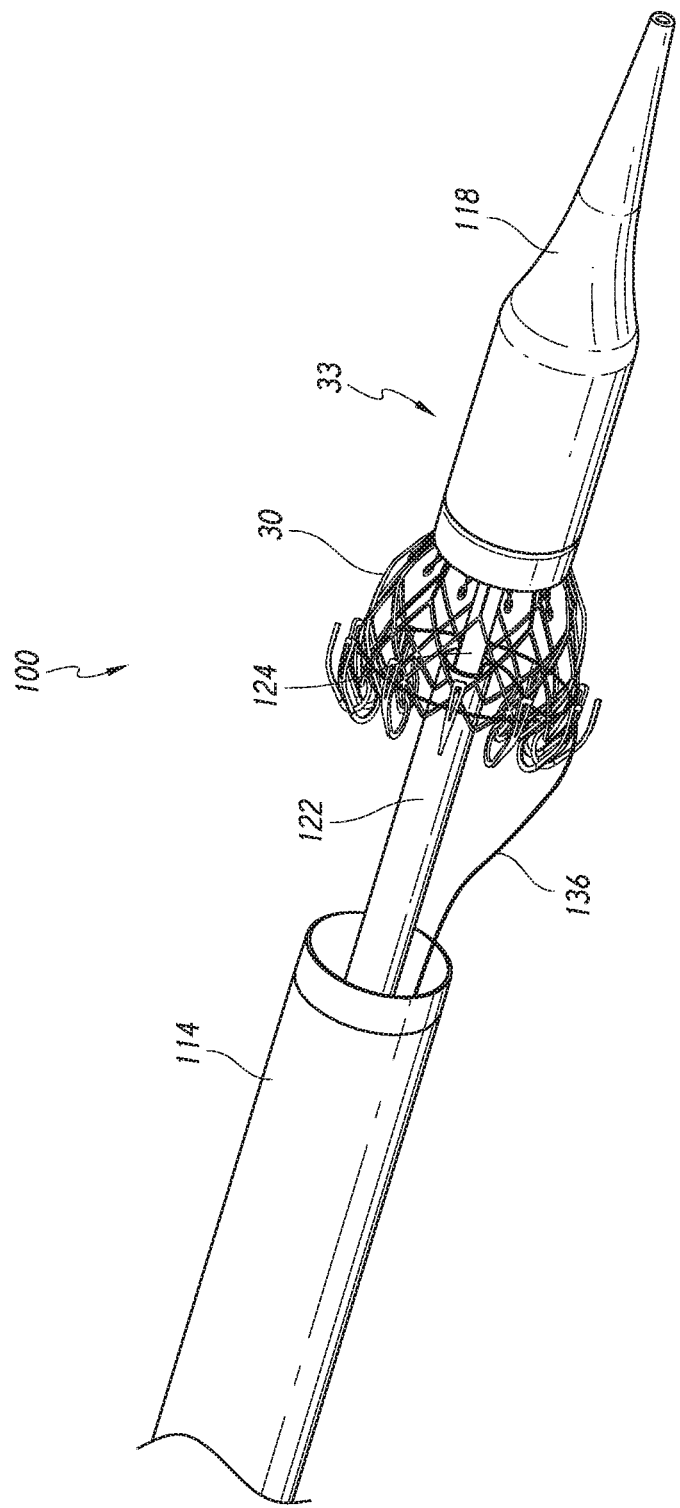

With reference next to the step of FIG. 8, the outer elongate hollow member shaft 114 can be further moved relatively away from the nose cone 118 to further uncover the implant 30. As shown in the illustrated embodiment, the second end of the implant 30 has been uncovered with the tether 136 being the only component restraining the radial dimension of the frame of the implant 30. By maintaining tension on the tether 136, the tether 136 can continue to at least partially restrain the radial dimension of the second end and can advantageously reduce the speed at which the second end radially expands. The tether 136 can be continuously released by the user at the handle 110 until the second end 14 of the implant 30 is fully expanded. In some embodiments, the tether 136 can be configured such that the first end 12 remains in the fully compacted state when the second end 14 is fully uncovered.

It should be noted that the first end 12 of the implant 30 can remain covered by the nose cone 118 during this step such that the first end 12 remains in a radially compacted state. Moreover, as shown in the illustrated embodiment, the second end 14 of the implant 30 has at least partially expanded in the radial dimension with the ventricular anchors 80 having been flipped to extend distally away from the second end of the implant 30 (and distally away from the handle 110). By controlling the expansion of the second end 14 of the implant 30 with the tether 136, the user can minimize the risk of the ventricular anchors 80 catching on surrounding tissue when the ventricular anchors 80 flip from extending proximally to extending distally.

Figure 9:
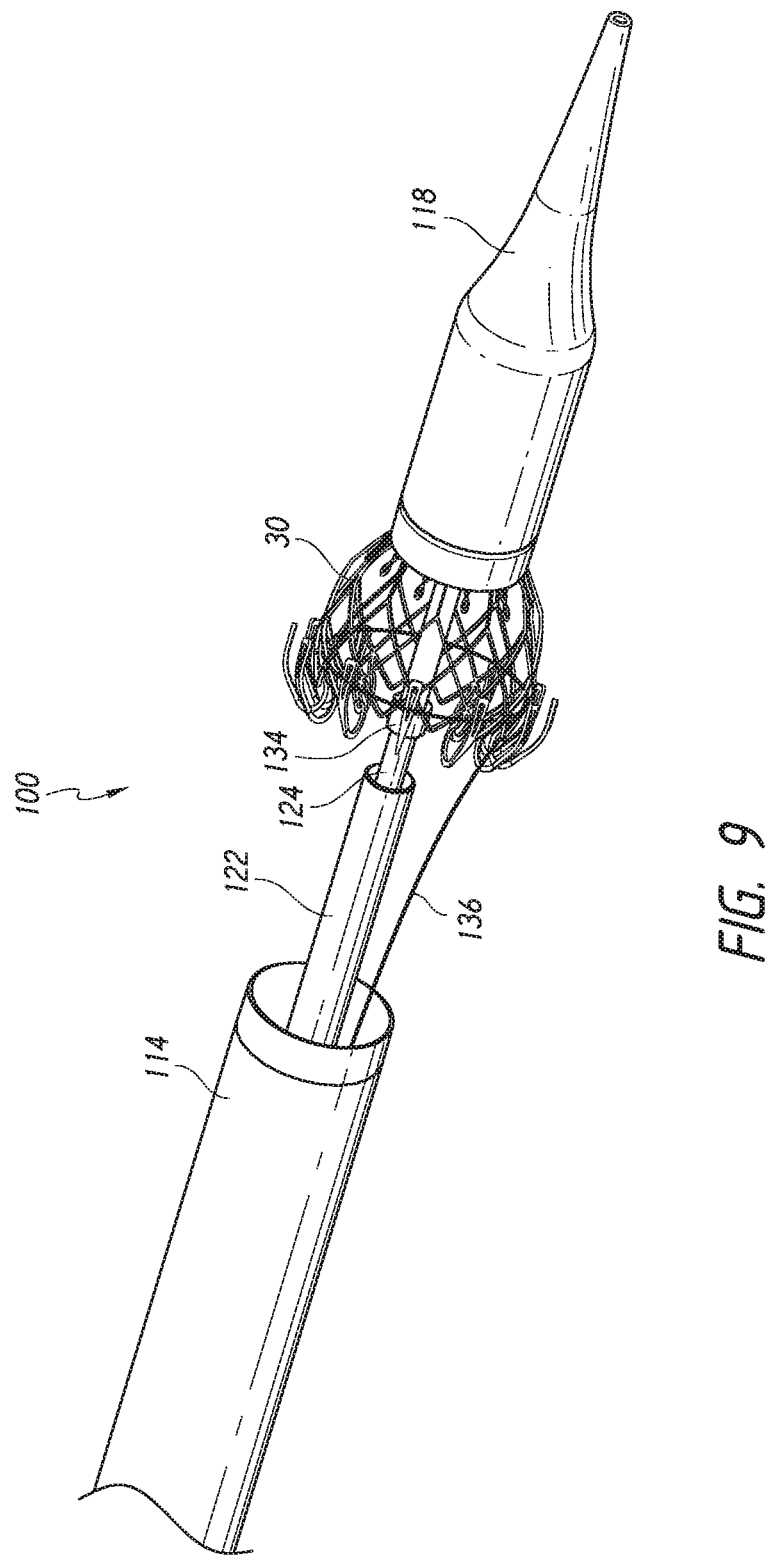

As shown in FIG. 9, once the second end 14 of the implant 30 is fully expanded, the locking shaft 122 can be moved relatively proximally to expose the tether retention member 134, thus allowing the tether 136 to fully release from the tether retention member 134.

Figure 10:
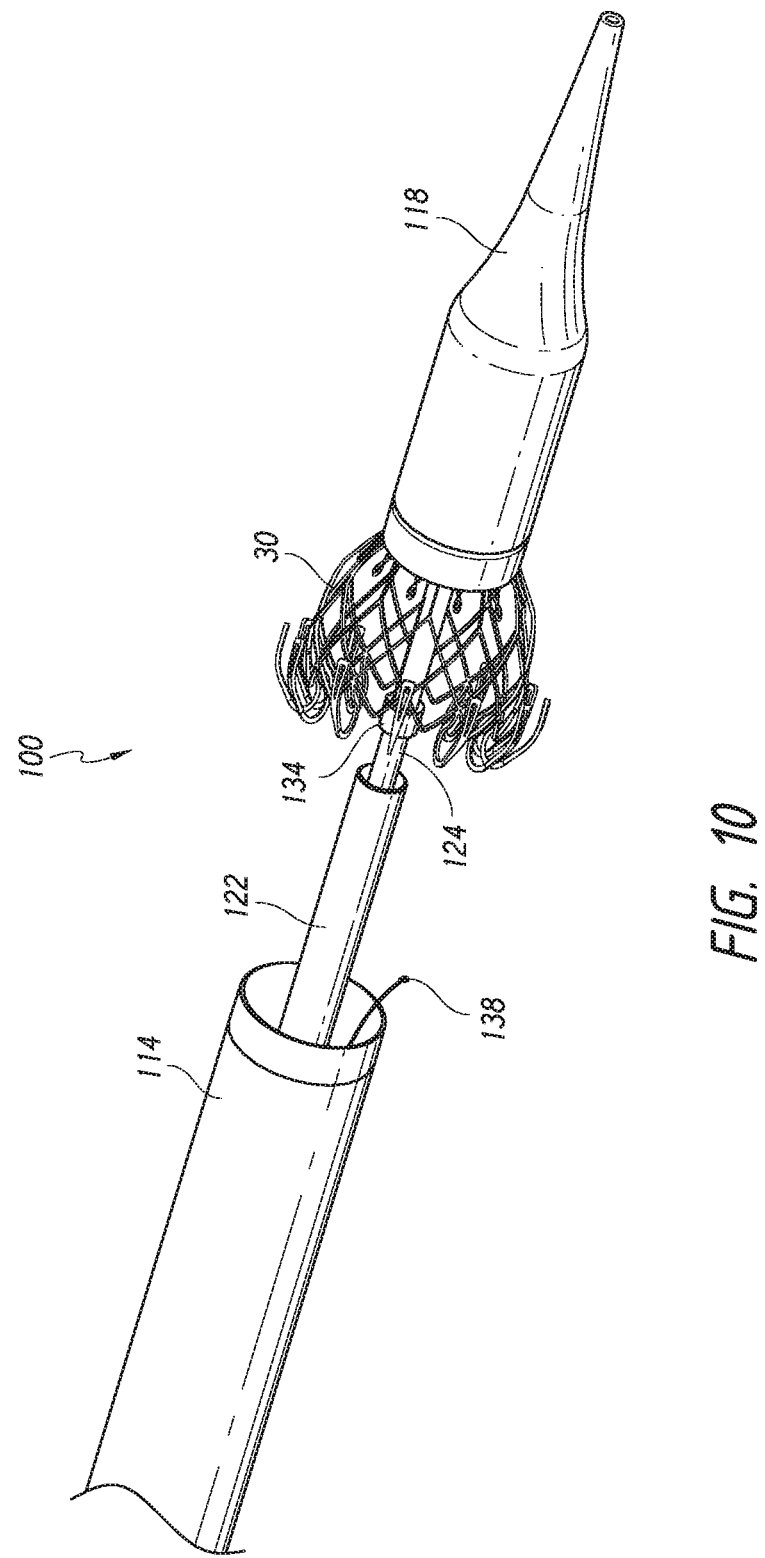

Next, as shown in FIG. 10, the tether retention member 134 has released the end 138 of the tether 136. It should be noted that the first end of the implant 30 can remain covered by the nose cone 118 during this step such that the first end remains in a radially compacted state. As discussed below, the tether 136 and end 138 can be retracted proximally into the delivery system 100 at this point.

Figure 11:
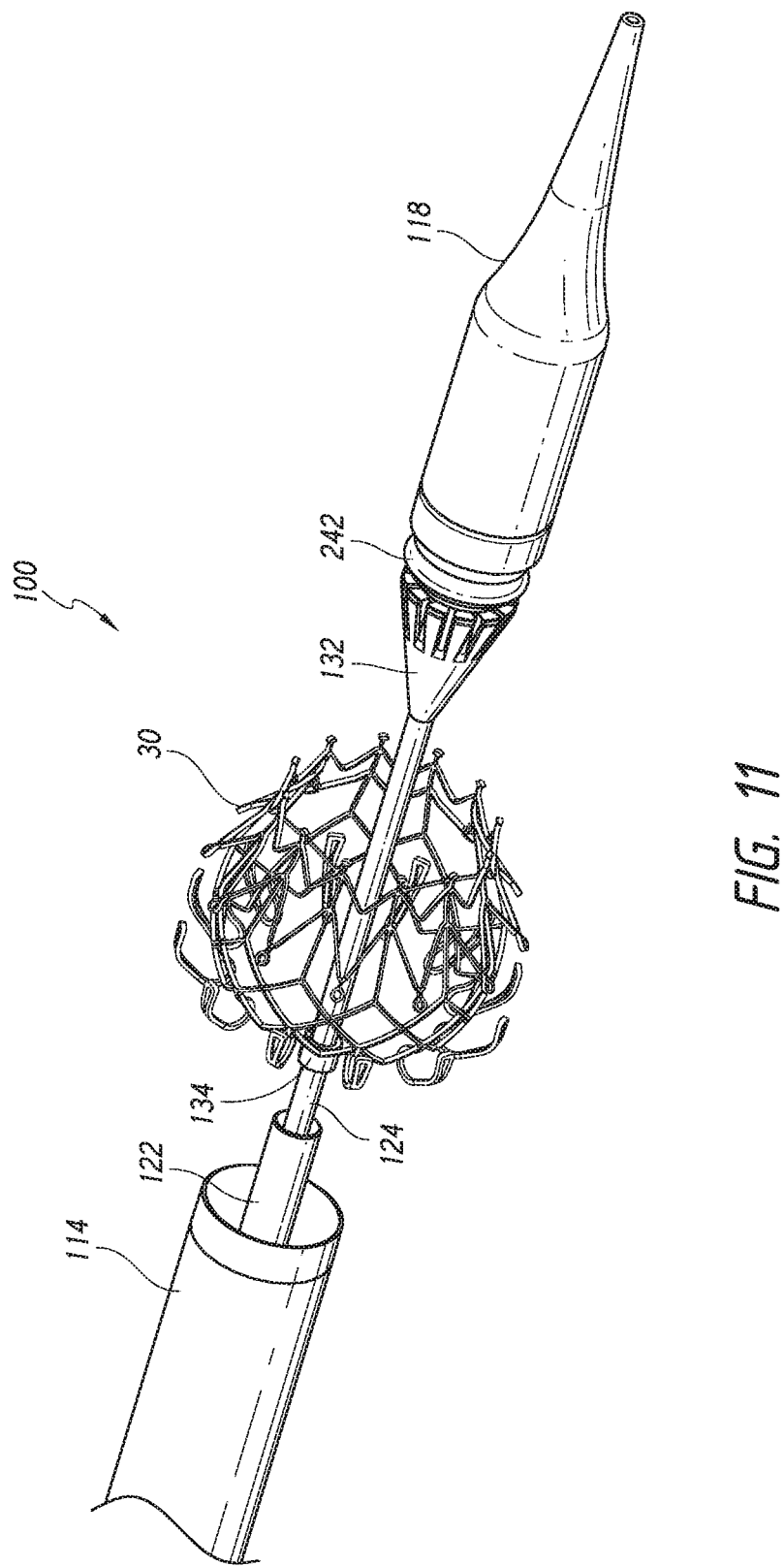

With reference next to the step of FIG. 11, the inner retention member 132 can be moved relatively away from the nose cone 118 such that the first end of the implant 30 can radially expand to its fully expanded configuration. This can be achieved by either distally moving the nose cone 118 relative to the inner retention member 132 and/or moving the inner retention member 132 proximally relative to the nose cone 118. After expansion and release of the implant 30, the inner retention member 132 and the nose cone 118 can be withdrawn through the center of the implant 30 and into the outer elongate hollow member shaft 114. Advantageously, as shown and discussed above, the inner retention member 132 can be tapered on the proximal end in order to more easily slide into the outer elongate hollow member shaft 114. Prior to withdrawing, the nose cone shaft 130 can be translated proximally to abut again the distal end of the inner retention member 132, which provides a tapered surface for the nose cone 118 to enter the outer elongate hollow member shaft 114 as well. In some embodiments, the locking shaft 122, the inner retention shaft 124 and the nose cone shaft 130 are moved proximally together so that the inner retention member 132 enters the outer elongate hollow member shaft 114 and the nose cone 118 abuts the distal end of the outer elongate hollow member shaft 114, and then the delivery system 100 is removed from the patient The delivery device 100 may be provided to users with an implant 30 preinstalled, such as illustrated in FIG. 6. In other embodiments, the implant 30 can be loaded onto the delivery device 100 shortly before use, such as by a physician or nurse.

Handle

FIGS. 12-15 show embodiments of a handle 110 that can be used in conjunction with the delivery device 100 as discussed in detail above.

FIG. 12 shows an internal viewpoint of the handle 110 with half of the housing 500 (shown in FIG. 1) removed. As shown, the handle 110 can include an outer elongate hollow member shaft knob 501 for translating the outer elongate hollow member shaft 114 as discussed above.

Moving proximally, the housing 500 can contain a tether (or lasso) knob 502. The lasso knob 502 can be rotated in order to controllably expand the implant 30, to release the tether 136 from the implant 30, and to retract the tether 136 towards the handle 110, as discussed above. Advantageously, the implant 30 can be completely released from the tether 136 and the tether 136 can be retracted towards the handle 110 through rotation of the tether knob 502 in a single direction, thus eliminating confusion or mistakes from a user and simplifying the overall design of the handle 110.

As discussed above, in the undeployed position the tether 136 can be held tightly around the implant 30 so as to prevent expansion of the implant 30. Once the implant 30 is located in the proper position, the tether 136 can be loosened from the implant 30 by a user turning the tether knob 502. The tether 136 can be loosened through motion of the tether knob 502 which unspools tether 136 from a spool, which may be provided as a cavity in the tether knob 502 or elsewhere in the handle 110. Upon initial turning of the tether knob 502 by a user, more of the tether 136 can be released from the spool towards the distal end where the implant 30 is located. As the implant 30 is configured to self-expand radially outwards, the release of more tether 136 can allow the implant to controllably radially expand. A user can continue to turn the tether knob 502 to release more tether, thus allowing full expansion of the implant 30.

Further, as the tether knob 502 is rotated, the tether knob 502 pushes a tether engager 503 proximally (shown in FIG. 13 which includes part of a sleigh 512, discussed below, removed for clarity). The tether engager 503 can include a screw like component that mates with an internal surface of the tether knob 502. Thus, as the tether knob 502 rotates, the tether engager 503 will be translated in a linear direction. In some embodiments, the tether engager 503 is located in a distal position when the tether 136 is wrapped around the implant 30, and translates proximally.

As the tether engager 503 moves proximally, it can abut a tether block 509 which can occur once the implant 30 is fully expanded. Upon continued turning of the tether knob 502, the tether engager 503 will push the tether block 509 proximally. The tether block 509 is attached to or operably connected to the proximal end of the locking shaft 122, so that the locking shaft 122 will move proximally as the tether engager 503 is moved proximally. This proximal movement will expose the tether retention member 134 on the inner retention shaft 124. Thus, at this point, the tether 136 can release from the tether retention member 134. The tether 136 and tether engager 503 can move at different distances upon turning of the tether knob 502. For example, one turn of the tether knob 502 can translate the tether engager 503 about 1 inch while the tether 136 will move about 3.14 inches. Further, the tether engager 503 can de-couple from the tether knob 502 after a certain amount of turn (e.g., after the tether 136 is released) and thus the tether knob 502 can rotate freely without moving the tether engager 503 to retract the tether 136.

Advantageously, once the tether 136 is free of the tether retention member 134, it has been unspooled via the tether knob 502. Then, a user can continue to turn the tether knob 502 in the same direction as before to retract the tether 136 towards the handle 110, creating a parabolic motion of the tether 136 from release to retraction. Specifically, the tether knob 502 is turned in a single direction to release the spooled tether from the tether knob 502. Then, once the tether 136 is completely unspooled, continued motion of the tether knob 502 re-spools the tether 136 back into the cavity in the tether knob 502 or handle 110. Thus, the tether knob 502 can be turned in one direction to both release and retract the tether 136. The tether can be drawn through tether channels 504 in the handle 110 distal to the tether knob 502 and wrapped into a circumferential spool in the tether knob 502 to safely store away the tether. As mentioned above, the tether 136 can include a nitinol wire with a suture crimped on the distal end of the nitinol wire. This attachment can occur proximal to the centering ring 224 within the outer elongate hollow member shaft 114. Further, the tether 136 can include a crimp sleeve stop located on the nitinol wire portion of the tether 136, relatively near the attachment of the nitinol wire and the suture (for example approximately 1 inch away). The crimp sleeve stop can prevent full retraction of the tether 136 into the handle 110 by abutting against the handle 114, or components near the distal end of the handle 114, thus providing for a mechanical stop.

Moving to the proximal end of the handle 110, a nose cone knob 506 is shown which is configured to advance or retract the nose cone 118 upon turning by a user, discussed above. As the nose cone knob 506 is turned, a lead screw coupled to the nose cone knob 506 and nose cone shaft 130 can be translated to provide proximal and distal motion to the nose cone shaft 130.

In addition, as shown in FIGS. 12-13, the handle 110 can include a sleigh 512 located within the housing 500. Specifically, the sleigh (e.g., cradle or sled) 512 has a generally tubular shape that is received within the proximal end of the generally tubular housing 500. The outer diameter of the sleigh 512 can be less than the outer diameter of the housing 500. Further, the sleigh 512 has a hollow interior in which the proximal ends of the inner retention shaft 124, locking shaft 122, and the nose cone shaft 130 are attached to, whether directly or through an intermediate component.

The sleigh 512 is configured to move proximally within the housing 500 and distally back into the housing 500. Thus, by pulling the sleigh 512 proximally relative to the housing 500 to a proximal position shown in FIG. 16, the inner retention shaft 124, locking shaft 122, and nose cone shaft 130, and thus the nose cone 118 and inner retention member 132, can be pulled proximally in one motion. Therefore, these components can be pulled into the outer elongate hollow member shaft 114, which is attached to the housing 500, for ease of withdrawal from a patient. This allows for fewer complications in pulling the different elements through the center of the implant 30.

The handle 110 can further include sleigh lock 510 located between the nose cone knob 506 and tether knob 502. The sleigh lock 510 can be rotated approximately 180° in order to unlock and lock translational motion of the sleigh 512. Thus, when the sleigh lock 510 is activated, the sleigh 512 cannot be pulled proximally. However, upon release of the sleigh lock 510, the sleigh 512 can be pulled proximally. In some embodiments, a user can pull on the deactivated sleigh lock 510 to pull the sleigh 512 proximally.

Indicators can be used on the outer surface of the handle, such as incorporated into the housing 500, in order to provide a user with visual or auditory indications of the locations of certain parts of the system 100. For example, as shown in FIG. 12, a channel, slot or aperture 520 can pass through the housing 500 of the handle 110 around a proximal end of the tether engager 503. The tether engager 503 can further have a projection 522 on or near its proximalmost surface which can extend into the channel 520. Thus, as the tether engager 503 moves proximally through the turning of the tether knob 502, a user can see the location of the tether engager 503 based on the position on the projection 522. Further, the slot 520 can contain "speed bumps" 521 on an inside surface of the slot 520 that can provide for a click when the projection 522 passes over them, which can also provide feedback to a user on the actions taken at the distal end of the system 100. For example, the speed bumps can indicate when the tether 136 is fully expanded and when the tether engager 503 is about to release the tether 136 through movement of the locking shaft 122.

Figure 14:
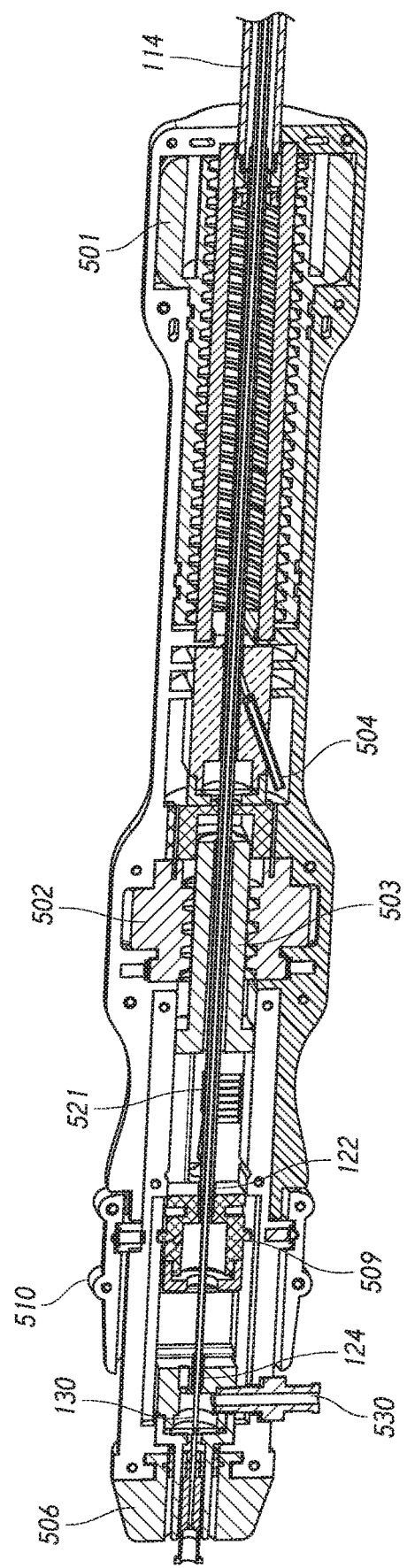
FIG. 14 illustrates a cross section of the handle of the delivery device.
Figure 15:
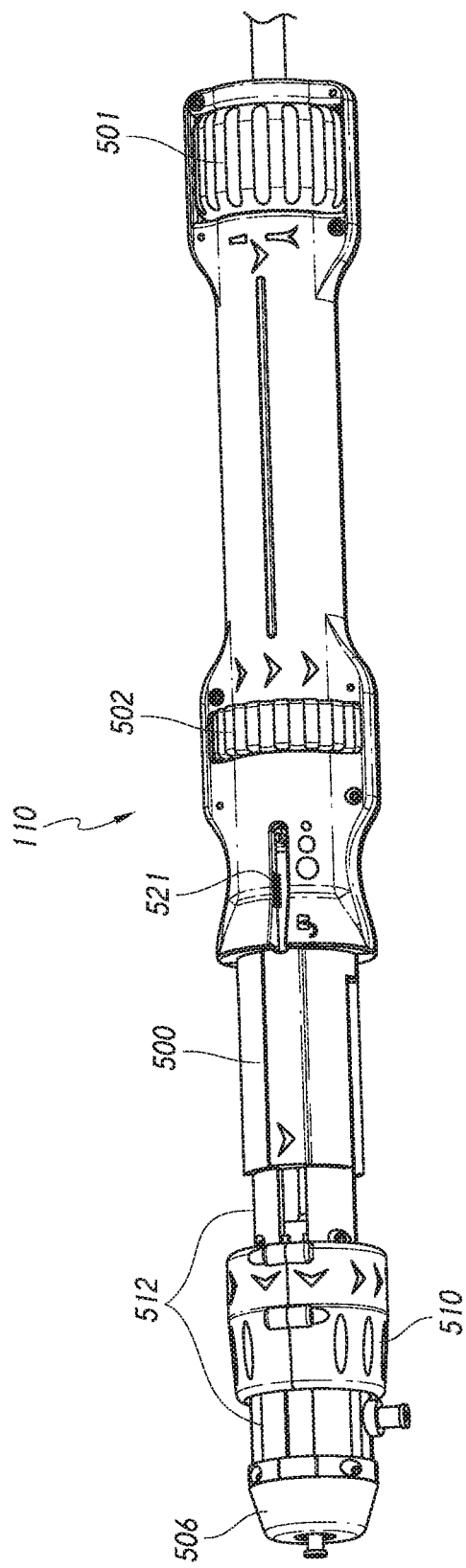
FIG. 15 illustrates translation of the unlocked sleigh in the handle.

Another aspect of the handle 110 is the single flush port 530 exposed outside the handle, which is shown in the cross-section of FIG. 14. The flush port 530 is fluidly connected to the inner retention shaft 124 and the locking shaft 122, thus allowing fluid to flush out both of those shafts so a second flush port is not needed. Further, the locking shaft 122 can include a plurality of radial apertures (not shown) on its proximal end outside of the handle. Advantageously, this allows fluid to pass from the locking shaft 122 and into the lumen formed by the outer elongate hollow member shaft 114. Thus, flushing through the single flush port 530 can provide fluid to the inner retention shaft 124, locking shaft 122, and the outer elongate hollow member shaft 114.

Insertion Methodology

Figure 16:
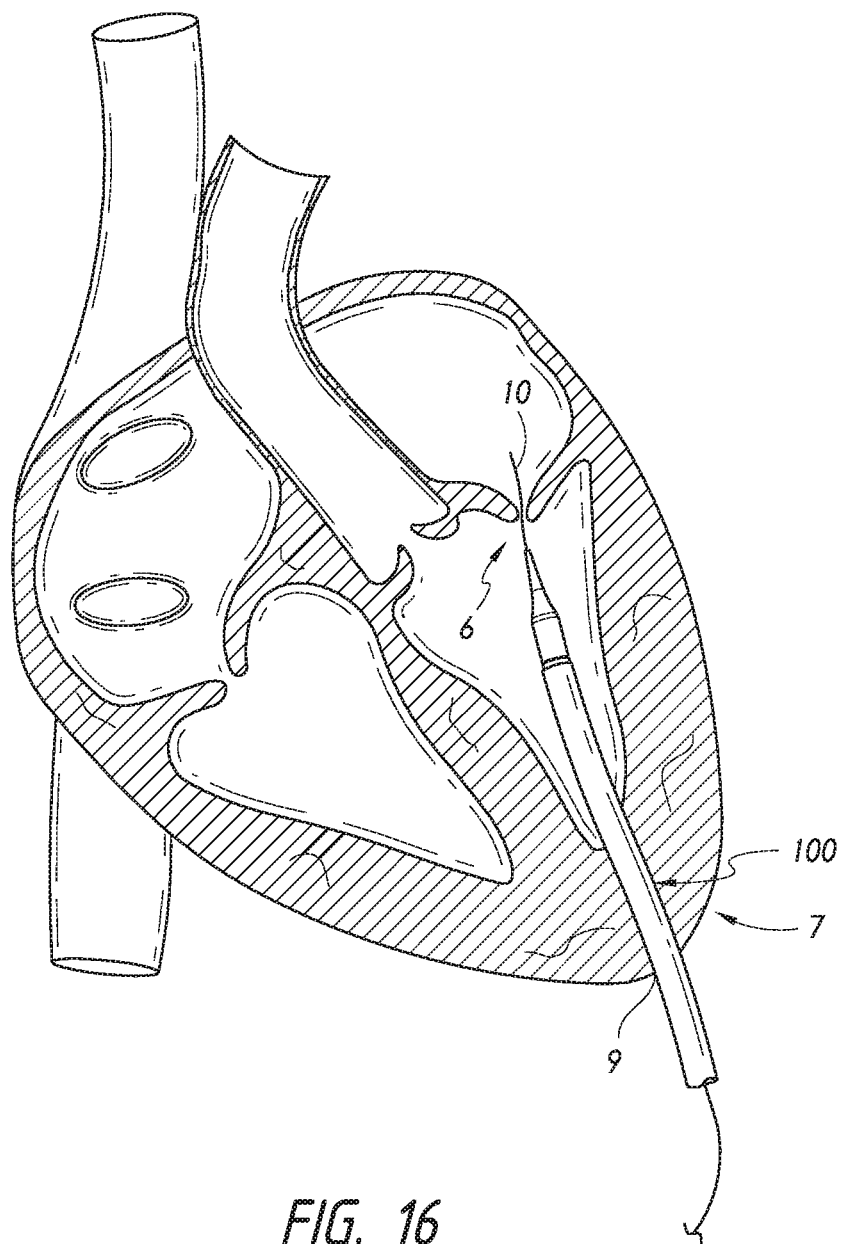
FIG. 16 illustrates a transapical approach for a delivery device.

FIG. 16 illustrates a transapical approach for use with the delivery device 100. As shown, the delivery device 100 can access a mitral valve through the apex 7 of the heart. As depicted in FIG. 16, a guidewire 10 is advanced into the left ventricle 6 of the heart through a puncture or opening 9 near the apex 7. The heart may be accessed through a limited thoracotomy, small trocar puncture, or small catheter puncture. With the guidewire 10 in place, the physician can insert the device 100 to the left ventricle 6 and deploy the heart valve as disclosed above. In some embodiments, a guidewire is not used.

Figure 17:
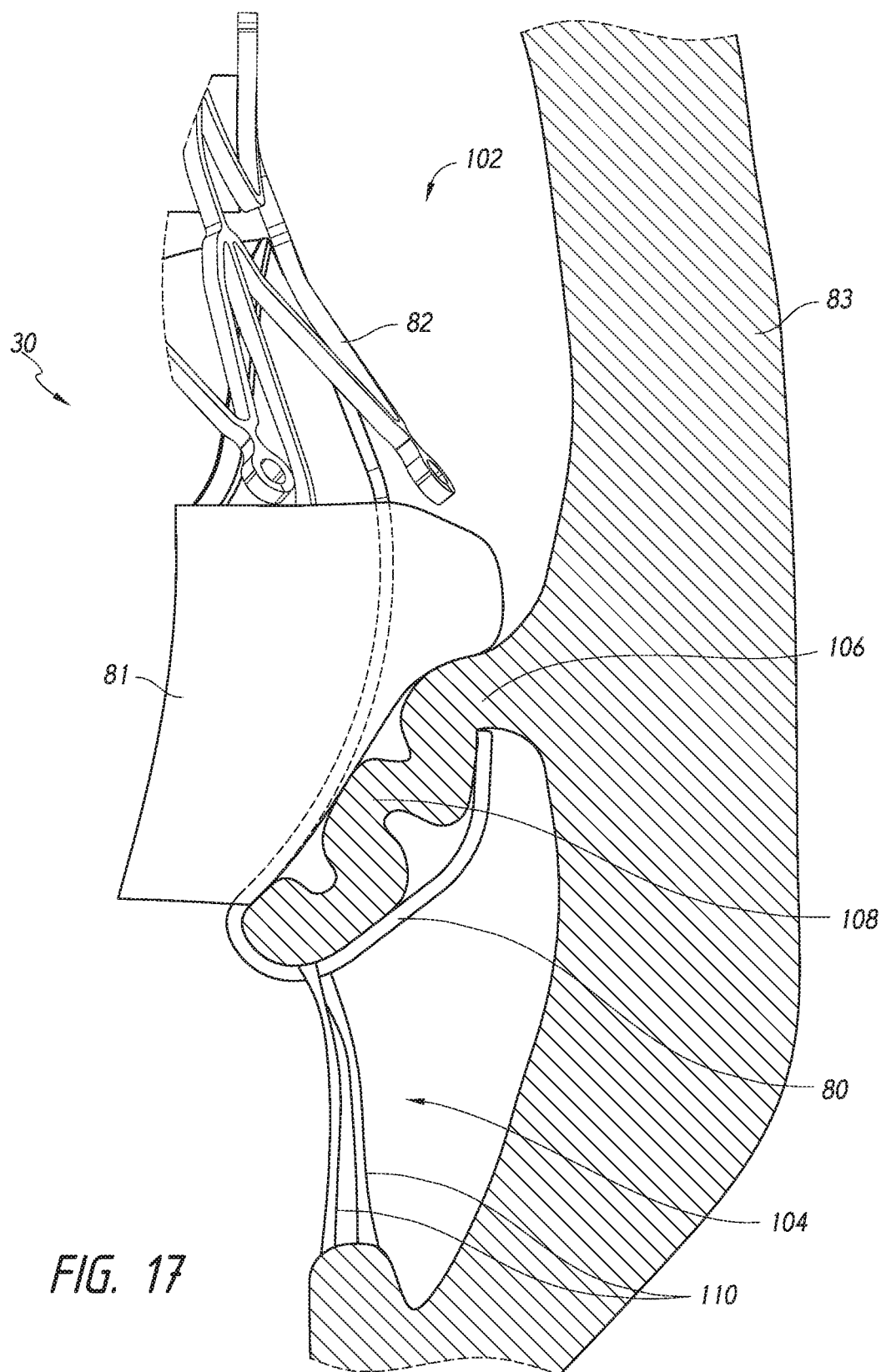
FIG. 17 illustrates a replacement heart valve implanted at the native mitral valve of a heart.

Reference is now made to FIG. 17 which illustrates a schematic representation of an embodiment of a replacement heart valve positioned within a native mitral valve of a heart 83. Further details regarding how the prosthesis 70 may be positioned at the native mitral valve are described in U.S. patent application Ser. No. 14/716,507, filed May 19, 2015, the entirety of which is hereby incorporated by reference, including but not limited to FIGS. 13A-15 and paragraphs [0036]-[0045]. A portion of the native mitral valve is shown schematically and represents typical anatomy, including a left atrium 102 positioned above the native mitral valve annulus 106 and a left ventricle 104 positioned below the annulus 106. The left atrium 102 and left ventricle 104 communicate with one another through the mitral annulus 106. Also shown schematically in FIG. 17 is a native mitral leaflet 108 having chordae tendineae 110 that connect a downstream end of the mitral leaflet 108 to the papillary muscle of the left ventricle 104. The portion of the implant 30 disposed upstream of the annulus 106 (toward the left atrium) can be referred to as being positioned supra-annularly. The portion generally within the annulus 106 is referred to as positioned intra-annularly. The portion downstream of the annulus 106 is referred to as being positioned sub-annularly (toward the left ventricle).

As illustrated in FIG. 17, the replacement heart valve (e.g., implant 30) can be disposed so that the mitral annulus 106 is between the ventricular anchors 80 and the atrial anchors 82. In some situations, the implant 30 can be positioned such that ends or tips of the ventricular anchors 80 contact the annulus 106. In some situations, the implant 30 can be positioned such that ends or tips of the ventricular anchors 80 do not contact the annulus 106. In some situations, the implant 30 can be positioned such that the ventricular anchors 80 do not extend around the leaflet 108.

The implant 30 can be positioned so that the ends or tips of the ventricular anchors 80 are on a ventricular side of the mitral annulus 106 and the ends or tips of the atrial anchors 82 are on an atrial side of the mitral annulus 106. The ventricular anchors 80 can be positioned such that the ends or tips of the ventricular anchors 80 are on a ventricular side of the native leaflets beyond a location where chordae tendineae 110 connect to free ends of the native leaflets. The ventricular anchors 80 may extend between at least some of the chordae tendineae 110 and, in some situations such as those shown in FIG. 17, can contact or engage a ventricular side of the annulus 106. It is also contemplated that in some situations, the ventricular anchors 80 may not contact the annulus 106, though the ventricular anchors 80 may still contact the native leaflet 108. In some situations, the ventricular anchors 80 can contact tissue of the left ventricle 104 beyond the annulus 106 and/or a ventricular side of the leaflets.

During delivery, the ventricular anchors 80 (along with the frame) can be moved toward the ventricular side of the annulus 106 with the ventricular anchors 80 extending between at least some of the chordae tendineae 110 to provide tension on the chordae tendineae 110. The degree of tension provided on the chordae tendineae 110 can differ. For example, little to no tension may be present in the chordae tendineae 110 if the leaflet 108 is shorter than or similar in size to the ventricular anchors 80. A greater degree of tension may be present in the chordae tendineae 110 where the leaflet 108 is longer than the ventricular anchors 80 and, as such, takes on a compacted form and is pulled toward the native valve annulus. An even greater degree of tension may be present in the chordae tendineae 110 where the leaflets 108 are even longer relative to the ventricular anchors 80. The leaflet 108 can be sufficiently long such that the ventricular anchors 80 do not contact the annulus 106.

The atrial anchors 82 can be positioned such that the ends or tips of the atrial anchors 82 are adjacent the atrial side of the annulus 106 and/or tissue of the left atrium 102 beyond the annulus 106. In some situations, some or all of the atrial anchors 82 may only occasionally contact or engage atrial side of the annulus 106 and/or tissue of the left atrium 102 beyond the annulus 106. For example, the atrial anchors 82 may be spaced from the atrial side of the annulus 106 and/or tissue of the left atrium 102 beyond the annulus 106. The atrial anchors 82 could provide axial stability for the implant 30. In some situations, some or all of the atrial anchors 82 may not contact an annular flap 81. This may occur when the annular flap 81 is in a collapsed configuration although it may also occur when the annular flap 81 is in an expanded configuration. In some situations, some or all of the atrial anchors 82 may contact the annular flap 81. This may occur when the annular flap 81 is in an expanded configuration although it may also occur when the annular flap 81 is in a collapsed configuration. It is also contemplated that some or all of the atrial anchors 82 may contact the atrial side of the annulus 106 and/or tissue of the left atrium 102 beyond the annulus 106

The annular flap 81 can be positioned such that a proximal portion of the annular flap 81 is positioned along or adjacent an atrial side of the annulus 106. The proximal portion can be positioned between the atrial side of the annulus 106 and the atrial anchors 82. The proximal portion can extend radially outward such that the annular flap 81 is positioned along or adjacent tissue of the left atrium 102 beyond the annulus 106. The annular flap 81 can create a seal over the atrial side of the annulus 106 when the flap 81 is in the expanded state. Further discussion on the annular flap 81 can be found in U.S. application Ser. No. 14/716,507, hereby incorporated by reference in its entirety.

Inflatable Nosecone Balloon

Disclosed herein are embodiments of a delivery system with an inflatable nosecone balloon that can advantageously reduce the time and necessary components for the transapical delivery of a replacement mitral valve.

In some transapical delivery methodologies for the implantation of a replacement mitral valve, generally a three step process may be used. First, a guidewire catheter is threaded through the left ventricle of the heart and into the left atrium to place a guidewire. Following, the guidewire catheter is removed and a balloon catheter is threaded onto the guidewire and a balloon is expanded in the left ventricle. The balloon is then passed from the left ventricle to the left atrium to determine whether the balloon passes smoothly between the two anatomical positions, indicating that the guide wire is not caught around chordae tendineae or other anatomical structures. The balloon is then removed and the delivery system is inserted along the guidewire.

However, the above-described procedure requires a number of different devices (e.g., delivery device, guidewire catheter, and balloon catheter) and requires the exchanging of different devices. These exchanges can lead to unwanted blood loss and can accidently misplace the guidewire during the removal and replacement of different devices. Further, the exchanging of device leads to a longer overall procedure time and can be costly with the need to have the plurality of devices.

Accordingly, embodiments of the disclosure are advantageous as they combine the features of multiple devices previously used into one easy-to-use delivery system. By eliminating the device exchange steps, the procedure time can be decreased, the blood loss can be decreased, and the device can be easier to implant.

Figure 18:
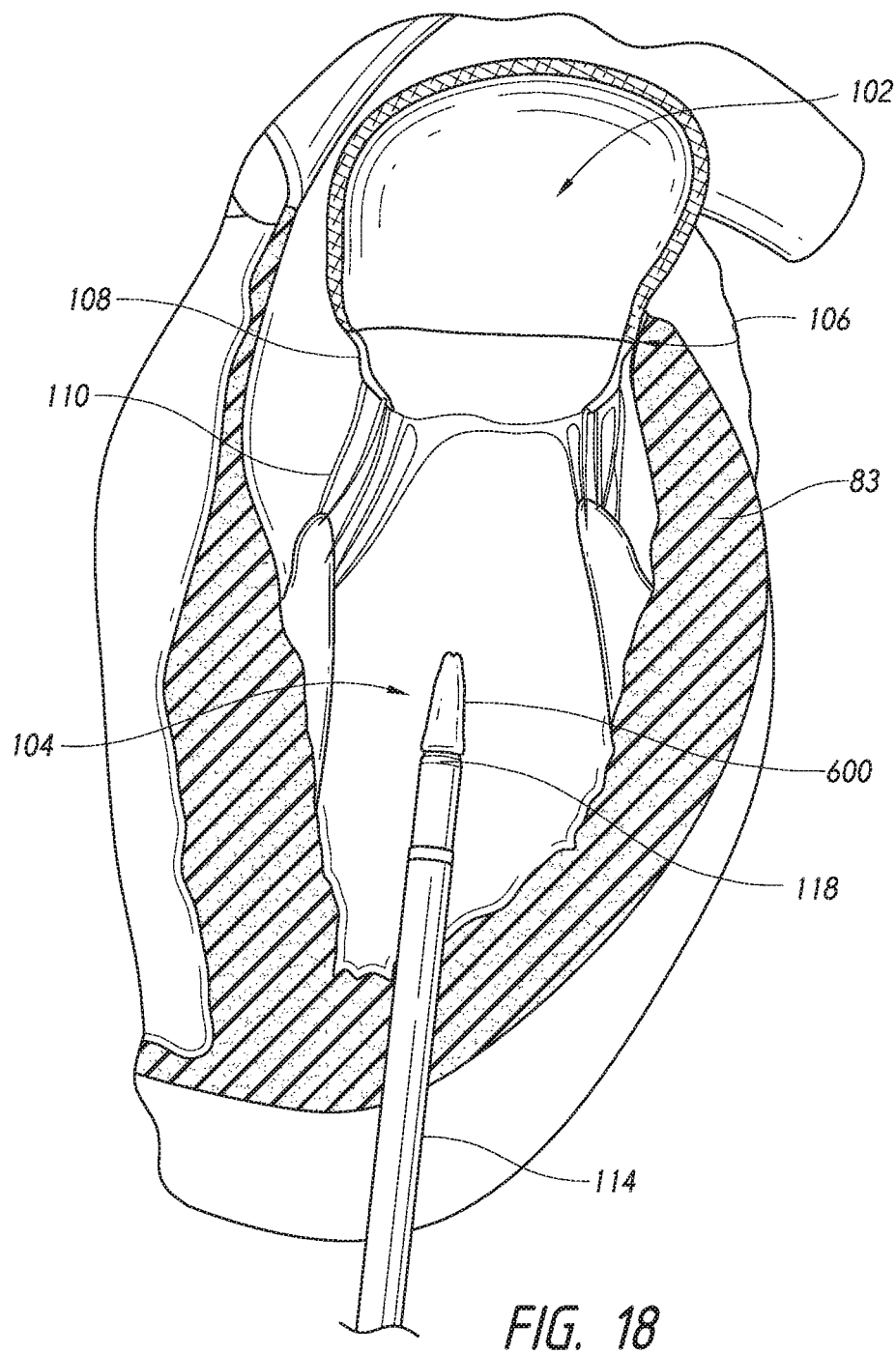
FIGS. 18-21 illustrate an inflatable nosecone balloon on a delivery system and a method of establishing a guidewire pathway without the use of an inflatable nosecone balloon.
Figure 19:
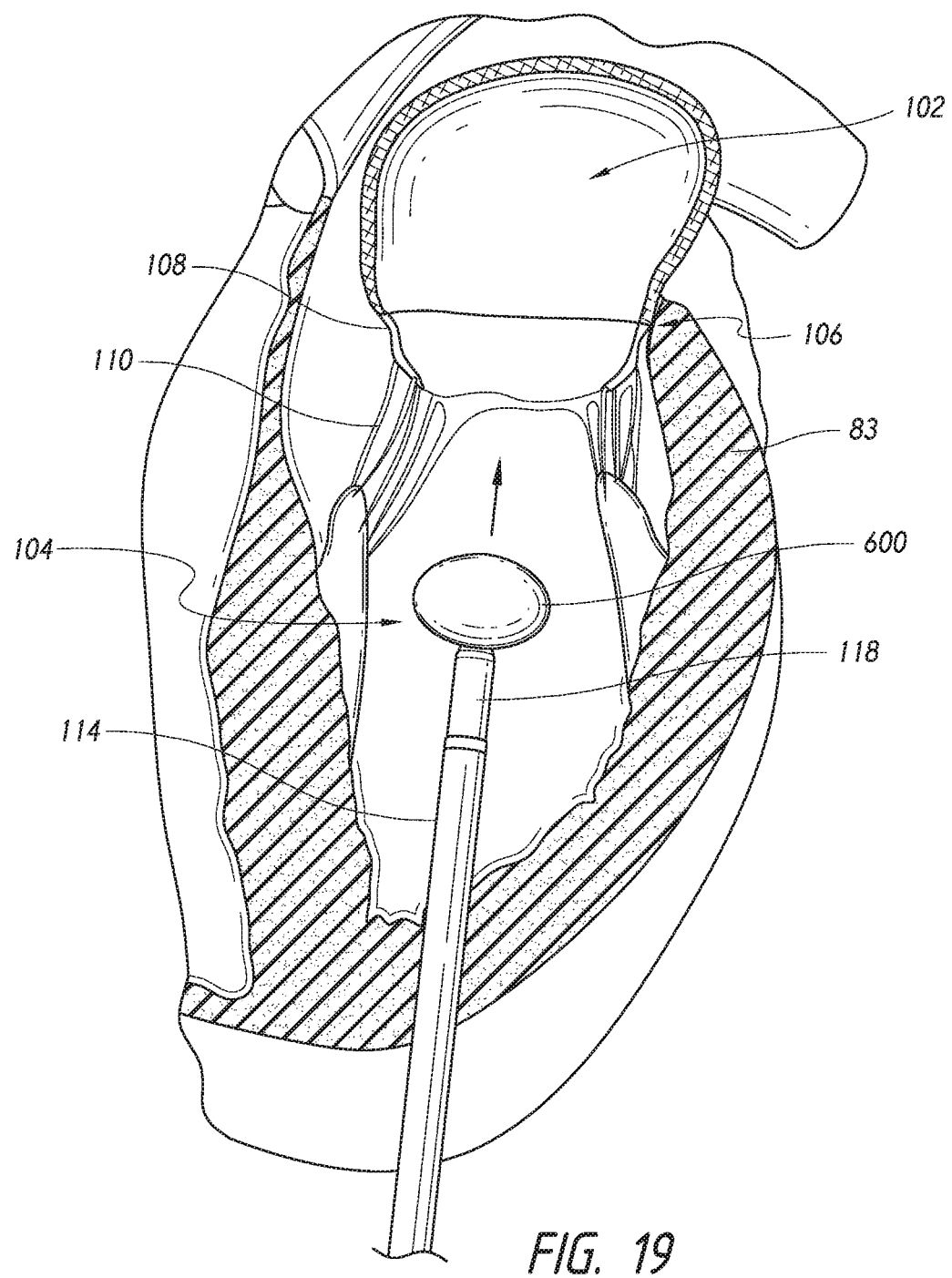
Figure 20:
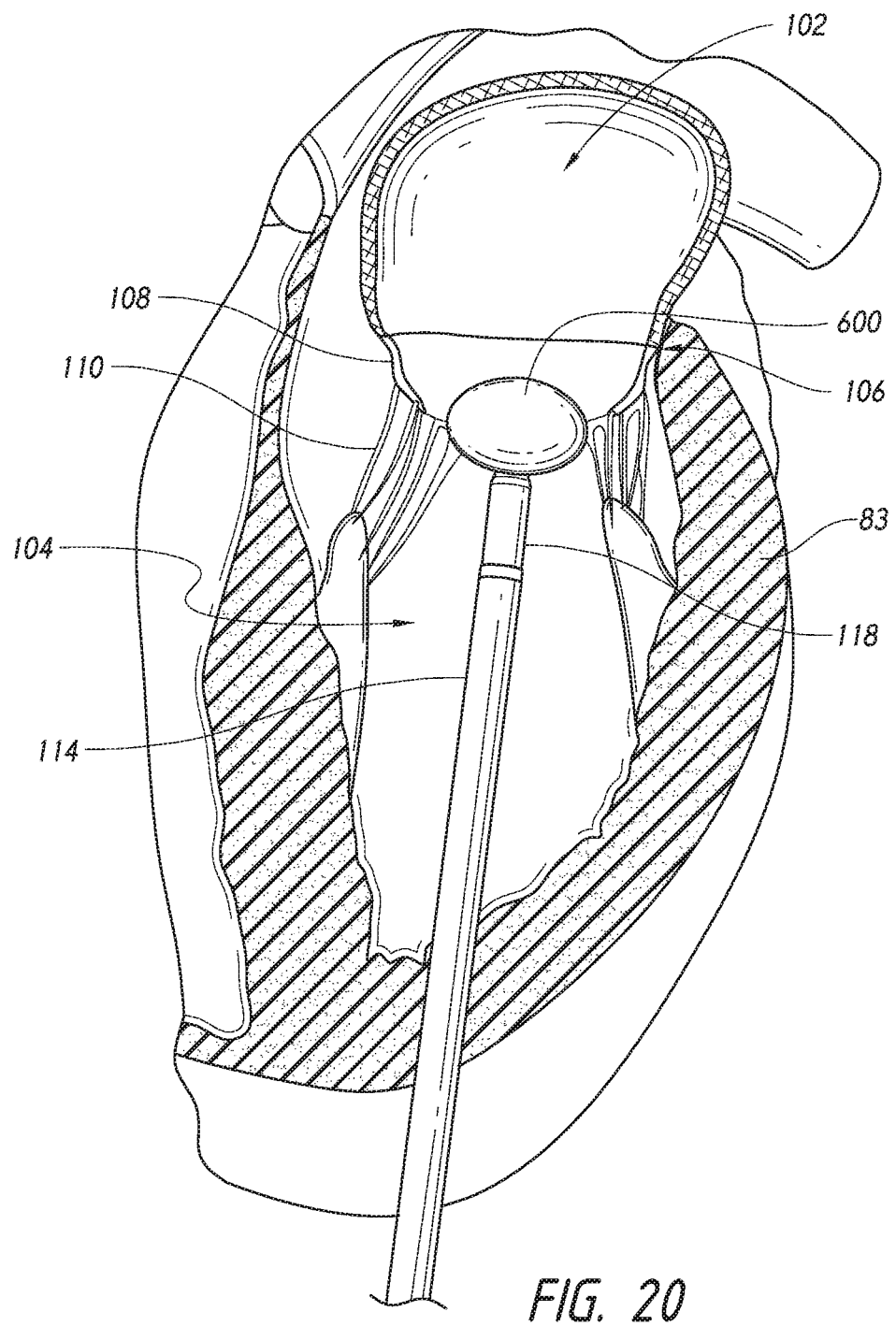
Figure 21:
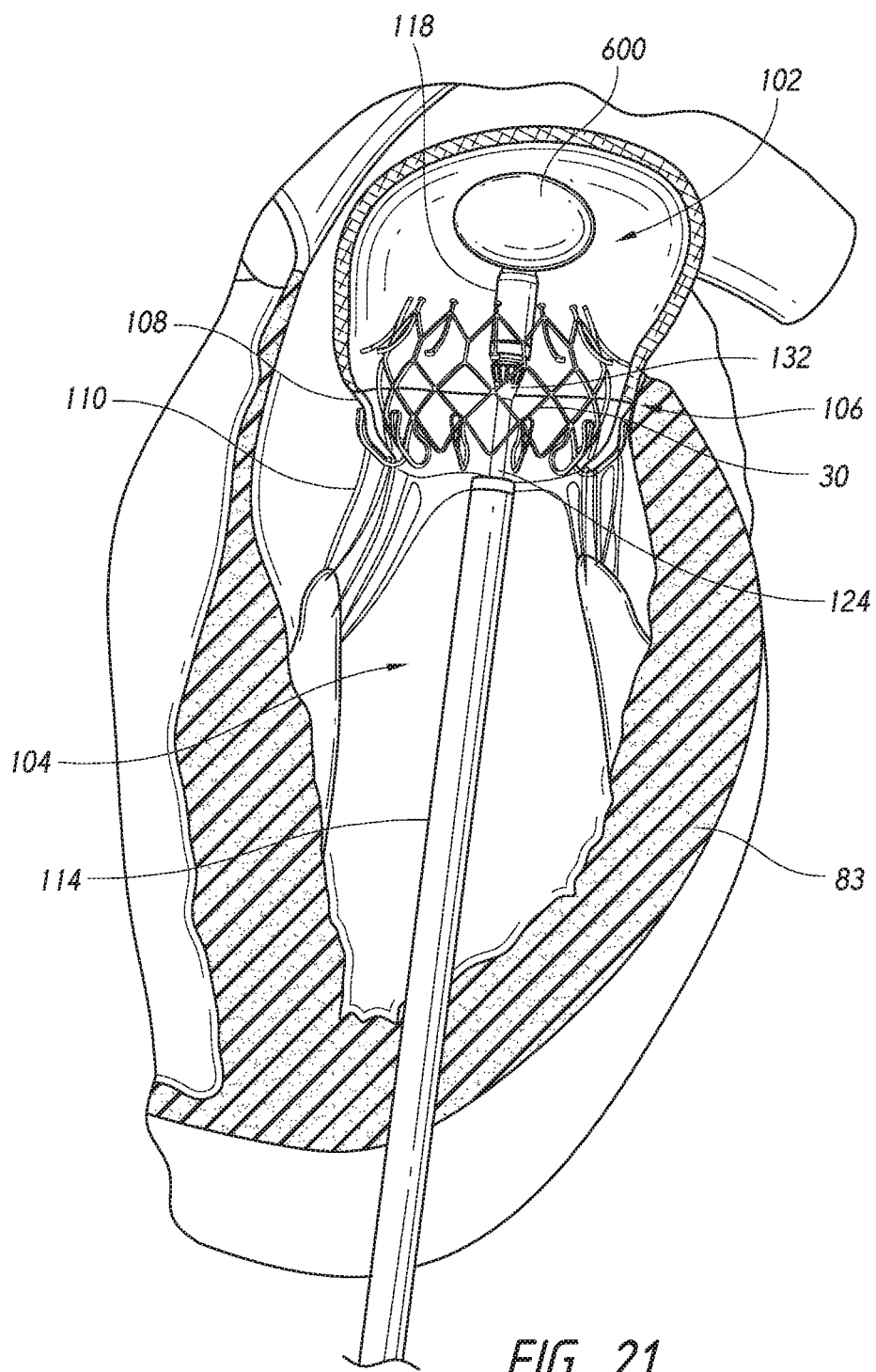

FIGS. 18-21 show an inflatable balloon 600 that can be incorporated into/around the nose cone 118 of a delivery system 100, such as disclosed in detail above. In some embodiments, the balloon 600 can be folded around the tapered tip of the nose cone 118 of the delivery system 100 in a deflated position, such as shown in FIG. 18. The balloon 600 can be expanded to form a generally toroidal or donut-shaped structure surrounding a portion of the nose cone 118 as shown in FIGS. 19-21. In some embodiments, the balloon 600 can extend distally past the distal tip of the nose cone 118. In some embodiments, a distal end of the balloon 600 can be approximately the same as the distal end of the nose cone 118. The balloon 600 can be made of rubber, polymer, or other material known for the creation of a balloon 600. In some embodiments, the balloon 600 can be located partially or fully proximal to the tapered tip of the nose cone 118.

The balloon 600 can be adhered chemically or mechanically to the nose cone 118 so that the balloon 600 remains around the nose cone 118 in the deflated and inflated position. However, in some embodiments the balloon 600 may only be attached to a distal end of the nose cone 118 and thus may extend distal to the distal end of the nose cone 118. In some embodiments, the nose cone 118 may contain grooves or indentations on its outer surface that the balloon 600 can fit into when in the folded/deflated position. This can provide a smoother transition for better apical crossing.

When in the deflated position, as shown in FIG. 18, the balloon 600 can lay along the nose cone 118 to form a generally atraumatic surface, typically in a tapered area of the nose cone 118. The balloon 600 can wrap around an external surface of the nose cone 118. The balloon 600 can further attach to a distal tip of the nose cone 118, which allows the balloon 600 to be in fluid communication with a lumen in the nose cone shaft 130. Accordingly, the lumen of the nose cone shaft 130 can extend proximally to an inflation source to inflate the balloon 600.

If a smoother profile is desired, a small outer sheath (not shown) may cover the balloon 600. In some embodiments, the outer elongate hollow member shaft 114 can cover the balloon 600 while in the deflated position, either partially or fully. Once the balloon 600 is in the left ventricle 104, as discussed below, this sheath can then be pulled proximally and the balloon 600 can be inflated.

In some embodiments, a separate inflation lumen can be used to inflate the balloon 600, which can run parallel, or approximately parallel, to the guide wire lumen in the nose cone shaft 130. In some embodiments, the guidewire lumen can be eliminated and/or replaced with the inflation lumen as no guidewire may be required. By removing the guidewire lumen, the overall dimensions of the delivery system 100 can be reduced. The inflation lumen can be significantly smaller than the guide wire lumen, and thus the overall distal profile of the delivery system 100 can be reduced.

FIG. 18-21 illustrate steps of an example of a delivery method using embodiments of the disclosed delivery system 100. As shown in FIG. 18, the distal end of the delivery system 100, including the deflated balloon 600, can be advanced through a hole in the apex of the heart 83 and into the left ventricle 104. The balloon 600 can then be expanded, such as to approximately 5, 10, 15, 20, 25, or 30 mm in diameter, once in the left ventricle 106 as shown in FIG. 19. However, other balloon dimensions can be used as well, and the particular inflation diameter is not limiting. The delivery system 100 can then be advanced through the mitral annulus 106 and towards the left atrium 102 as shown in FIG. 20, which ensures that the delivery system 100 does not get trapped/entangled within the chorea tendineae 110, mitral valve leaflets 108, or other anatomic structures. Once located in the left atrium 100, the implant 30 can be released per the above disclosure while the balloon 600 remains inflated as shown in FIG. 21, though only the frame of the implant 30 is shown. The implant 30 show is discussed in detail in U.S. patent application Ser. No. 15/141,684, filed Apr. 28, 2016, but other implants discussed herein can be used as well. The balloon 600 can be advanced atrially so it does not occlude any blood flow through the mitral valve. If no guidewire is being used, once the balloon 600 is advanced past the native mitral annulus 106, the balloon 600 can be left inflated (or partially inflated) which will hold the distal end of the delivery system 100 in the left atrium 102. In some embodiments, the balloon 600 can be further inflated in the left atrium 102. Once the implant 30 is positioned, the balloon 600 can be deflated and the delivery system 100 can be withdrawn from the heart 83.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A delivery system for controlled deployment of a collapsible implant, the delivery system comprising:
   a handle at a proximal end of the delivery system, the handle comprising a tether control knob configured to control movement of a tether extending distally away from the handle; and
   an outer hollow member operably connected to the handle configured to at least partially restrain the implant in a collapsible configuration, wherein the tether extends through the outer hollow member to engage the implant when the implant is positioned within the outer hollow member, the outer hollow member being moveable relative to the implant to expose the implant at a body location while the tether keeps the implant radially restrained;
   an inner shaft extending through the outer hollow member;
   a tether retention member located on the inner shaft proximal to where the tether engages the implant, the tether retention member configured to hold a free end of the tether;

a locking shaft slidable over the inner shaft and the tether retention member;
a block located within the handle and proximal of the tether control knob, the block attached to a proximal end of the locking shaft;
wherein rotation of the tether control knob in a single direction initially unspools the tether for allowing radial expansion of the implant;
wherein after the radial expansion of the implant, further rotation of the tether control knob in the single direction translates a screw in the handle proximally to translate the block and the locking shaft proximally away from the tether retention member to release the free end of the tether; and
wherein after the release of the free end of the tether, further rotation of the tether control knob in the single direction retracts the tether proximally through the outer hollow member toward the handle and respools the tether.

2. The delivery system of claim 1, wherein the tether is configured to unspool and spool in a cavity within the tether control knob.

3. The delivery system of claim 1, further comprising a replacement valve located within a distal portion of the outer hollow member, wherein the tether wraps around the replacement valve to prevent expansion of the replacement valve.

4. The delivery system of claim 1, wherein the tether retention member comprises a c-lock, the c-lock having a longitudinal slot covered by the locking shaft, the slot retaining the free end of the tether.

5. The delivery system of claim 4, further comprising a centering ring on the locking shaft to center the locking shaft within the outer hollow member, the centering ring comprising at least one aperture through which the tether passes.

6. The delivery system of claim 1, wherein the handle comprises an auditory or visual indicator to provide a user a signal indicating a position of the tether.

7. A delivery system for controlled deployment of a collapsible replacement heart valve, the delivery system comprising:
a handle comprising an outer housing and a generally tubular shaped sleigh located at least partially within the outer housing and received within a proximal end of the outer housing, the sleigh having a hollow interior;
a first elongate shaft operably connected to the housing and configured to cover at least a proximal end of the collapsible replacement heart valve;
a second elongate shaft located within the first elongate shaft and operably connected to the hollow interior of the sleigh at a proximal end of the second elongate shaft;
a third elongate shaft located within the second elongate shaft and operably connected to the hollow interior of the sleigh at a proximal end of the third elongate shaft;
a fourth elongate shaft located within the third elongate shaft and having a nose cone on a distal end thereof, the nose cone configured to radially restrain a distal end of the collapsible replacement heart valve, the fourth elongate shaft is operably connected to the hollow interior of the sleigh at a proximal end of the fourth elongate shaft; and
a single flush port exposed outside of the handle, wherein the single flush port is fluidly connected to the first elongate shaft, the second elongate shaft, and the third elongate shaft;
wherein the sleigh is configured to translate relative to the housing from a distal to a proximal position, wherein translation of the sleigh from the distal to the proximal position translates the second, third, and fourth elongate shafts proximally in one motion so that the second, third, and fourth elongate shafts remain in the same position relative to one another in the distal and proximal position during the in one motion translation of the sleigh from the distal to the proximal position; and
wherein the handle comprises a sleigh lock configured to prevent motion of the sleigh upon activation of the lock.

8. The delivery system of claim 7, further comprising a first shaft knob configured to translate the first elongate shaft distally and proximally, a second shaft knob configured to translate the second elongate shaft distally and proximally, and a fourth shaft knob configured to translate the fourth shaft distally and proximally, wherein each of the shaft knobs can move their respective shafts independent of one another.

9. The delivery system of claim 7, wherein the sleigh extends proximally from the handle in the proximal position.

10. A delivery system for controlled deployment of a collapsible replacement heart valve, the delivery system comprising:
a handle comprising an outer housing and a generally tubular shaped sleigh located at least partially within the outer housing and received within a proximal end of the outer housing, the sleigh having a hollow interior;
a first elongate shaft operably connected to the housing and configured to cover at least a proximal end of the collapsible replacement heart valve;
a first shaft knob configured to translate the first elongate shaft distally and proximally;
a second elongate shaft located within the first elongate shaft and operably connected to the hollow interior of the sleigh at a proximal end of the second elongate shaft;
a second shaft knob configured to translate the second elongate shaft distally and proximally;
a third elongate shaft located within the second elongate shaft and operably connected to the hollow interior of the sleigh at a proximal end of the third elongate shaft;
a fourth elongate shaft located within the third elongate shaft and having a nose cone on a distal end thereof, the nose cone configured to radially restrain a distal end of the collapsible replacement heart valve, the fourth elongate shaft is operably connected to the hollow interior of the sleigh at a proximal end of the fourth elongate shaft;
a fourth shaft knob configured to translate the fourth shaft distally and proximally, wherein each of the first shaft knob, the second shaft knob, and the fourth shaft knob are configured to move their respective shafts independent of one another; and
a single flush port exposed outside of the handle, wherein the single flush port is fluidly connected to the first elongate shaft, the second elongate shaft, and the third elongate shaft;
wherein the sleigh is configured to translate relative to the housing from a distal to a proximal position, wherein translation of the sleigh from the distal to the proximal position translates the second, third, and fourth elongate shafts proximally in one motion so that the second, third, and fourth elongate shafts remain in the same position relative to one another in the distal and proximal position during the in one motion translation of the sleigh from the distal to the proximal position.

11. The delivery system of claim 10, wherein the handle comprises a sleigh lock configured to prevent motion of the sleigh upon activation of the lock.

12. The delivery system of claim 10, wherein the sleigh extends proximally from the handle in the proximal position.

* * * * *